United States Patent
Almquist et al.

(10) Patent No.: US 11,058,632 B2
(45) Date of Patent: Jul. 13, 2021

(54) DRUG DELIVERY USING APTAMER CONSTRUCT

(71) Applicant: IMPERIAL COLLEGE INNOVATIONS LIMITED, London (GB)

(72) Inventors: Benjamin David Almquist, London (GB); Anna Stejskalova, London (GB)

(73) Assignee: Imperial College Innovations Limited, London (GB)

(*) Notice: Subject to any disclaimer, the term of this patent is extended or adjusted under 35 U.S.C. 154(b) by 0 days.

(21) Appl. No.: 16/333,982

(22) PCT Filed: Sep. 20, 2017

(86) PCT No.: PCT/GB2017/052795
§ 371 (c)(1),
(2) Date: Mar. 15, 2019

(87) PCT Pub. No.: WO2018/055360
PCT Pub. Date: Mar. 29, 2018

(65) Prior Publication Data
US 2019/0254958 A1    Aug. 22, 2019

(30) Foreign Application Priority Data
Sep. 20, 2016   (GB) ..................................... 1615989

(51) Int. Cl.
| | |
|---|---|
| *A61K 47/51* | (2017.01) |
| *A61K 9/00* | (2006.01) |
| *A61P 17/02* | (2006.01) |
| *A61P 35/00* | (2006.01) |
| *A61K 31/7105* | (2006.01) |
| *A61K 31/711* | (2006.01) |
| *A61K 47/32* | (2006.01) |
| *A61K 47/34* | (2017.01) |
| *A61K 47/42* | (2017.01) |
| *C12N 15/115* | (2010.01) |

(52) U.S. Cl.
CPC .......... *A61K 9/0024* (2013.01); *A61K 31/711* (2013.01); *A61K 31/7105* (2013.01); *A61K 47/32* (2013.01); *A61K 47/34* (2013.01); *A61K 47/42* (2013.01); *A61K 47/51* (2017.08); *A61P 17/02* (2018.01); *A61P 35/00* (2018.01); *C12N 15/115* (2013.01); *C12N 2310/16* (2013.01); *C12N 2310/3519* (2013.01); *C12N 2320/30* (2013.01); *C12N 2320/32* (2013.01)

(58) Field of Classification Search
CPC .. A61K 9/0024; A61K 47/51; A61K 31/7105; A61K 31/711; A61K 47/32; A61K 47/34; A61K 47/42; A61P 17/02; A61P 35/00; C12N 15/115; C12N 2320/30; C12N 2320/32; C12N 2310/3519; C12N 2310/16
See application file for complete search history.

(56) References Cited

FOREIGN PATENT DOCUMENTS

| | | |
|---|---|---|
| EP | 1793006 | 6/2007 |
| WO | 1996027604 | 9/1996 |
| WO | 1997009068 | 4/1997 |
| WO | 2011091307 | 7/2011 |

OTHER PUBLICATIONS

Alibolandi et al., (2015), "In vitroandin vivoevaluation of therapy targeting epithelial-cell adhesion-molecule aptamers for non-small cell lung cancer", Journal of Controlled Release, 209:88-100.
Danesh Noor Mohammad, et al., (2015), "Targeted and controlled release delivery of daunorubicin to T-cell acute lymphoblastic leukemia by aptamer-modified gold nanoparticles", International Journal of Pharmaceutics, 489(1):311-317.
Chushak, Yaroslav and Stone, Morley O., (2009) "In silico selection of RNA aptamers", Nucleic Acids Research, 37(12):1-9.
Convery, Maire A., et al., (1998) "Crystal structure of an RNA aptamer-protein complex at 2.8 A resolution", Nature Structural Biology, 5(2):133-139.
Hamada, Michiaki, (2018) "In silico approaches to RNA aptamer design", Biochimie, 145:8-14.
Huang, De-Bin, et al., (2003) "Crystal structure of NF-kB (p50)2 complexed to a high-affinity RNA aptamer", PNAS, 100(16):9268-9273.
Jarvis, Thale C., et al., (2015) "Non-helical DNA Triplex Forms a Unique Aptamer Scaffold for High Affinity Recognition of Nerve Growth Factor", Structure, 23:1293-1304.
Long, Stephen B., et al., (2008) "Crystal structure of an RNA aptamer bound to thrombin", RNA, 14:2504-2512.
Nimjee, Shahid M., (2017) "Aptamers as Therapeutics", Annu. Rev. Pharmacol. Toxicol., 57:61-79.
Oberthuer, Dominik, et al., (2015) "Crystal structure of a mirror-image L-RNA aptamer (Spiegelmer) in complex with the natural L-protein target CCL2", Nature Communications, 6(6923):1-11.

(Continued)

*Primary Examiner* — J. E. Angell
(74) *Attorney, Agent, or Firm* — Carol L. Francis; Bozicevic, Field & Francis LLP

(57) ABSTRACT

A molecular complex comprising a therapeutic agent and a controlled release construct, the controlled release construct comprising a primary matrix conjugation site which is linked to an cell adhesive site, via a binding region and optionally via one or more spacer elements, wherein the binding region has a folded configuration in which it is bound to the therapeutic agent, wherein the construct is configured such that when mechanical tension is applied between the primary matrix conjugation site and the cell adhesive site, the binding region adopts a less folded configuration in which bound therapeutic agent is released. Related controlled release constructs for loading with the therapeutic agent, pharmaceutical compositions and methods of manufacture and use.

20 Claims, 29 Drawing Sheets
Specification includes a Sequence Listing.

(56) References Cited

OTHER PUBLICATIONS

Shcherbinin, Dmitrii S., et al., (2015) "Computer-aided design of aptamers for cytochrome p450", Journal of Structural Biology, 191:112-119.
Stejskalova, Anna et al., (2019) "Biologically Inspired, Cell-Selective Release of Aptamer-Trapped Growth Factors by Traction Forces", Adv. Mater, 31:1-8.
Zhou, Jiehua and Rossi, John, (2017) "Aptamers as targeted therapeutics: current potential and challenges", Nature Reviews Drug Discovery, 16:181-203.

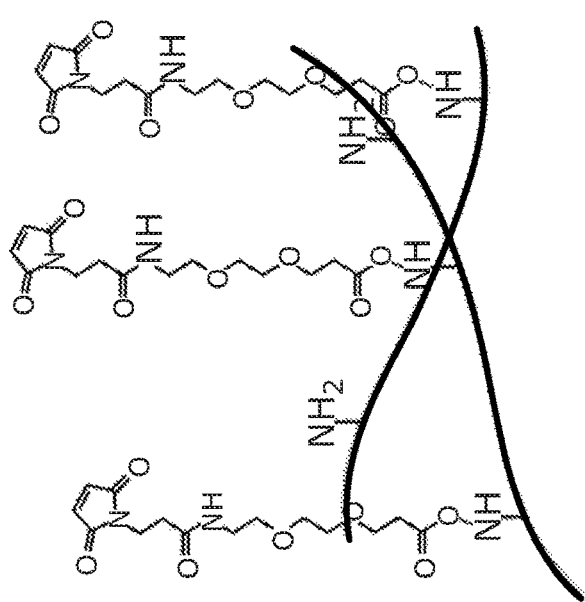
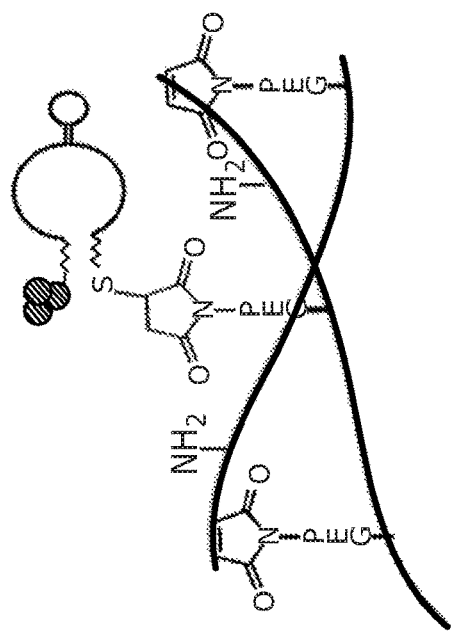
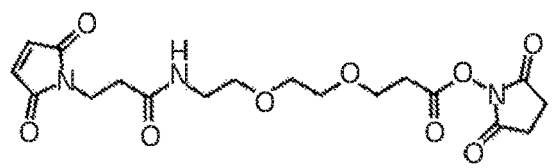
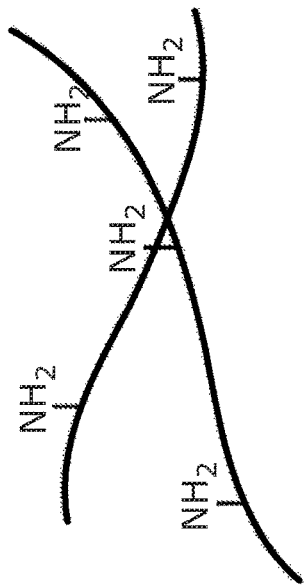
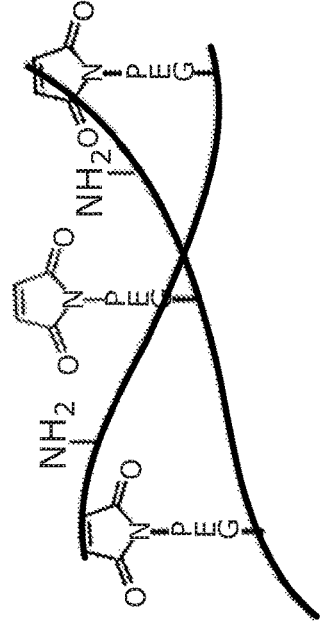
Fig. 4(i)
Fig. 4(ii)

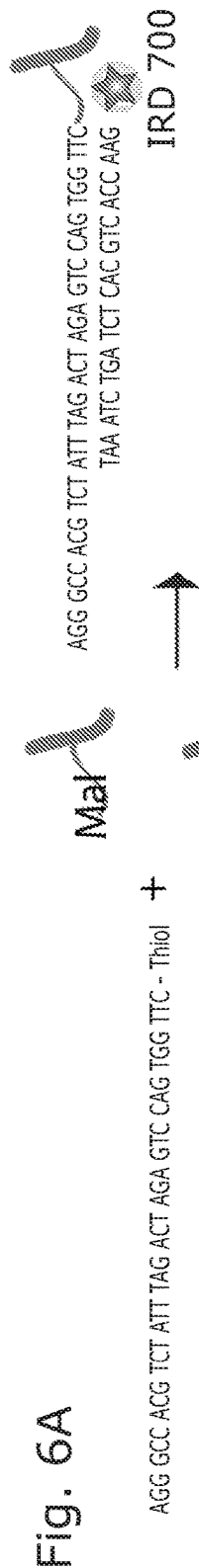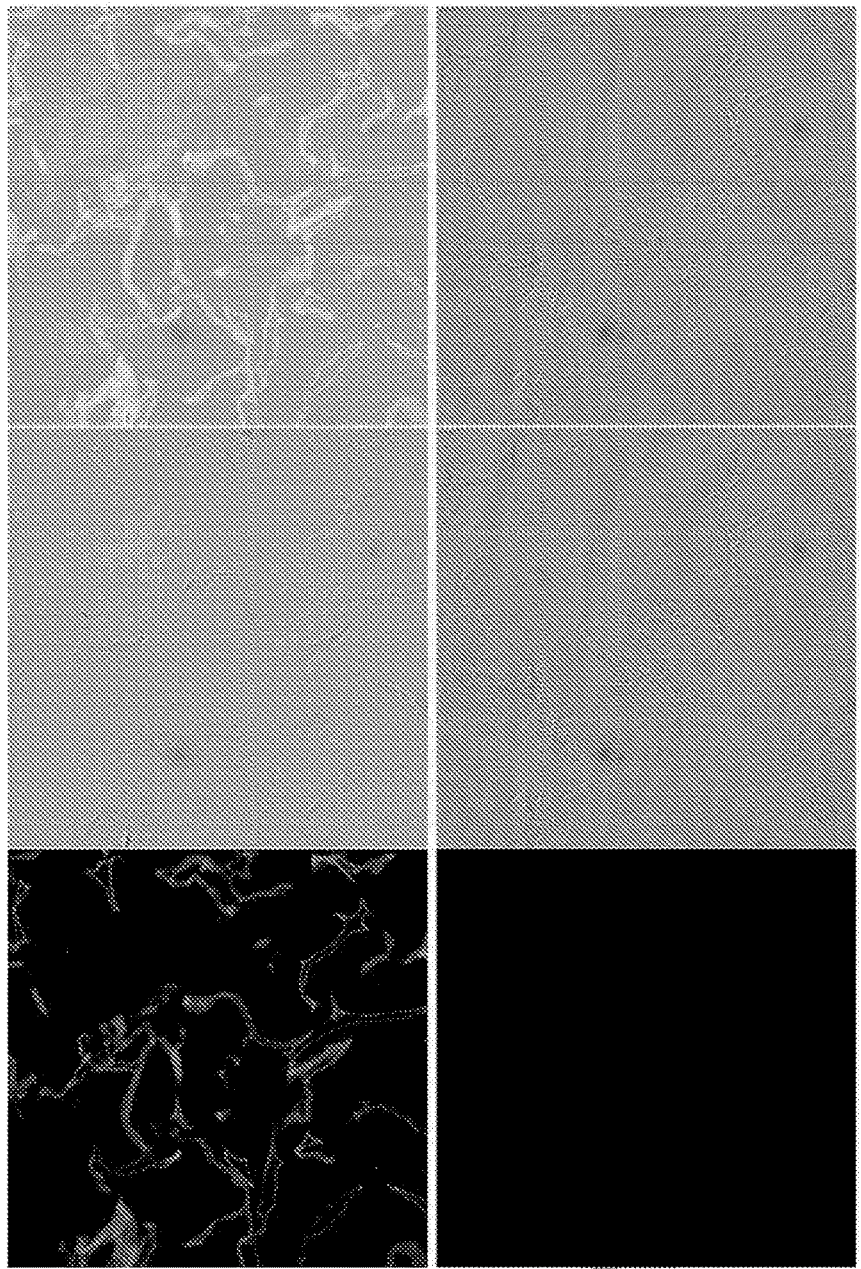
Fig. 6A
Fig. 6B

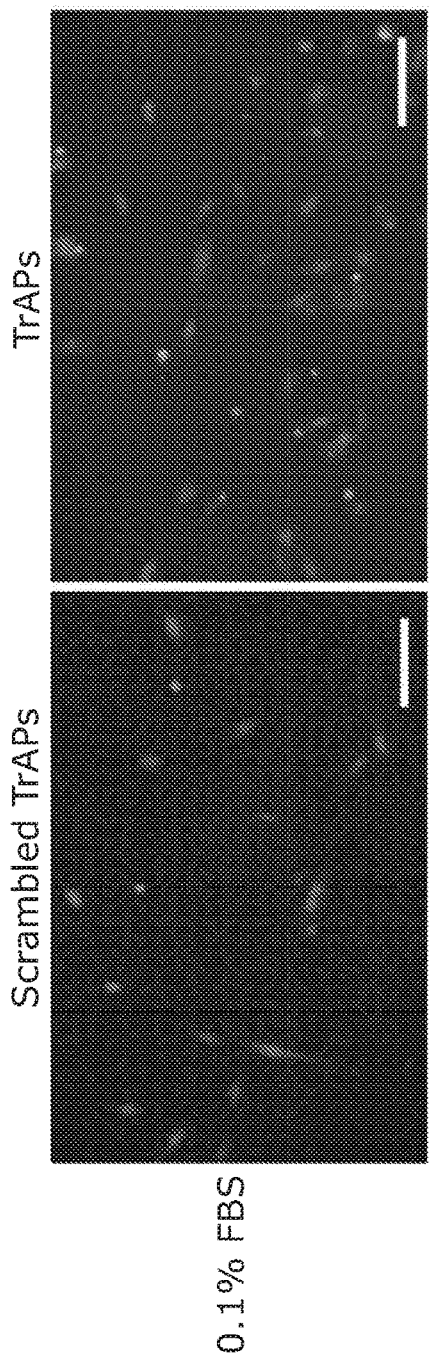
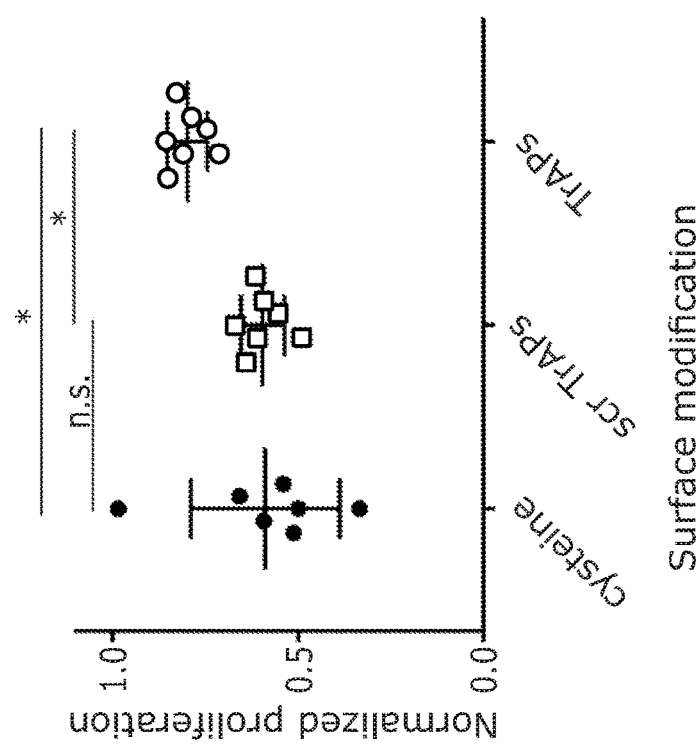
Fig. 8A
Fig. 8B

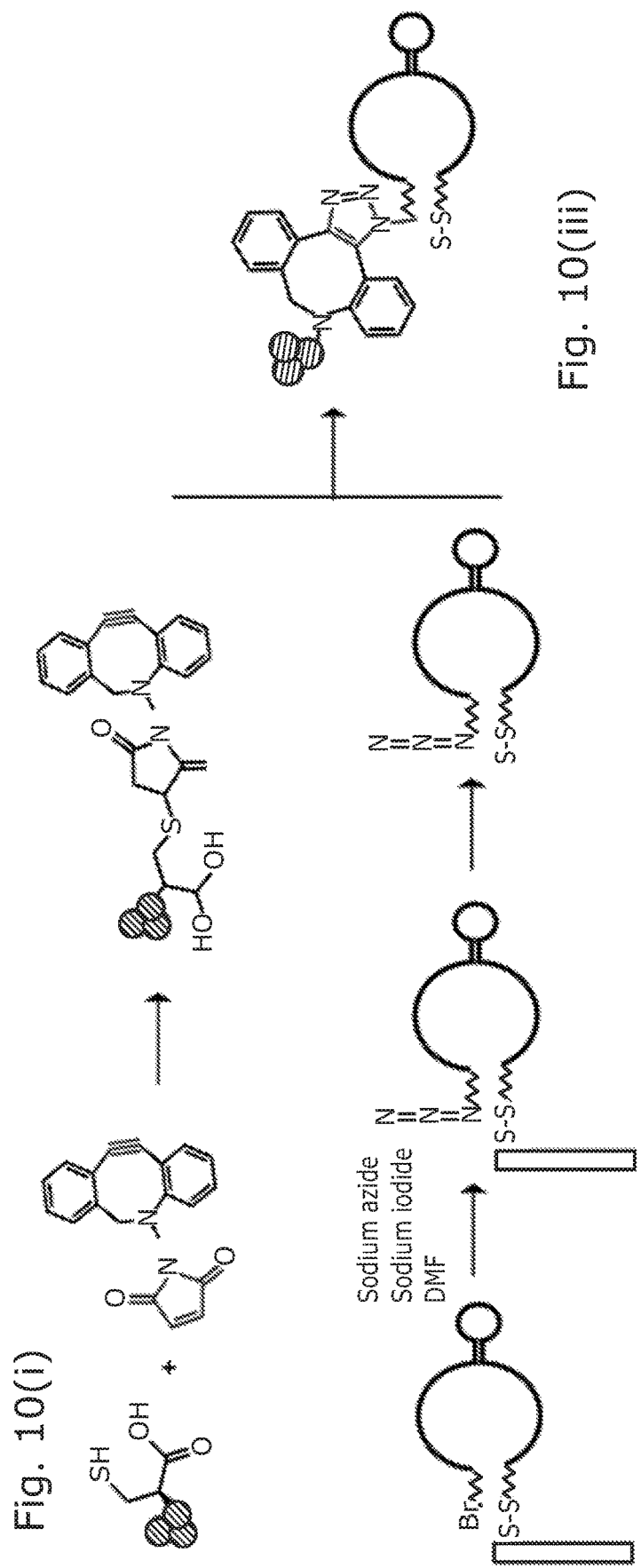

| Compound | MW |
|---|---|
| Maleimide-DBCO | 427.45 |
| GRGDSP | 690.73 |
| GRGDSP | 690.73 |
| cyclo(Arg-Gly-Asp-D-Phe-Cys) | 578.65 |
| cyclo(Arg-Ala-Asp-D-Phe-Lys) | 592.68 |
| TCEP | 250.19 (286.65), 266.1894 (oxygenated) |

Fig. 10(a)

|  | ng/μl | A260 | A280 | A260/280 | A260/230 |
|---|---|---|---|---|---|
| Thiol_PEG_VEGF_Az_1 | 667.6 | 20.229 | 12.405 | 1.63 | 1.97 |
| Thiol_PEG_VEGF_Az_2 | 850.1 | 25.761 | 15.721 | 1.64 | 2.01 |
| Thiol_PEG_VEGF_Az_3 | 1477 | 44.759 | 27.801 | 1.61 | 1.97 |
| Thiol_PEG_VEGF_Az_4 | 1227.1 | 37.184 | 22.689 | 1.64 | 2 |

NH$_2$ + Thiol-DNA

Maleimide + Thiol-DNA

Maleimide + Thiol-DNA + cysteine

DRUG DELIVERY USING APTAMER CONSTRUCT

BACKGROUND OF THE INVENTION

Local delivery of therapeutic agents including small molecule drugs and biologics has numerous advantages over systemic delivery. Furthermore, sustained and/or delayed release of a therapeutic agent at a local site has been shown to dramatically reduce the required dosage levels needed for therapeutic benefits, which can reduce the potential for detrimental side effects. One area where there is a particular need for improvement in local delivery is in the use of growth factors for the promotion of tissue repair. For instance, the INFUSE® bone graft product sold by Medtronic consists of an absorbable collagen sponge carrier (ACS) which contains recombinant human bone morphogenetic protein-2 (rhBMP-2). It is approved for use in stimulating local bone formation at the site to which the ACS is implanted. Although it is a successful product, the ACS is soaked with 1.5 mg of rhBMP-2, which is more BMP-2 than is naturally present in all the individuals within the hospital in which it is being administered and this must result in non-physiologically relevant levels of BMP-2 being present following initial placement of the sponge in vivo, followed by a rapid decline of BMP-2 concentrations as the therapeutic quickly diffuses away from the ACS.

There is much promise in the use of various growth factors, for example BMPs, FGFs and EGFs for the promotion of wound healing and also for in vitro tissue engineering. However, when administered on a traditional carrier matrix, or sprayed onto a wound or injected via a syringe to the wound site as has been proposed, the same problems of initial very high non-physiologically relevant concentrations, followed by a rapid decline in concentration and a low temporal persistence of the growth factor are encountered. Practical problems resulting from this may include side effects (from too high a dose), lack of efficiency (from subsequent too low a dose) and the need for many repeated doses (to maintain efficacy over time).

Related problems arise with cytotoxic drugs, for example those used to control cancer, in that ensuring that a sufficiently cytotoxic dose is received by the targeted cells, may result in exposing non-target cells to a dose sufficient to cause undesirable side effects.

Similar concerns arise with almost all classes of drugs where the challenges of delivery at the right concentration and to the right site in the body arise. Additionally, many drugs are incompletely specific for their molecular target. If they could be targeted to the correct tissue and/or cell type, even if that targeting was only partially specific, overall specificity would be advantageously increased.

To address those concerns, and others, the present invention relates to a technology that enables local sustained release of a therapeutic agent when direct cell contact with the delivery construct occurs, preferably within a target site.

Aptamers

Aptamers are oligonucleotide or peptide molecules, or derivatives/analogues thereof, that bind to a specific target molecule. They are typically produced by a selection process from a large and variable pool of sequences. Aptamers share some characteristics, such as strong binding affinity and specificity, with antibodies and have been proposed for use as therapeutics.

Pegaptanib (brand name Macugen®) is an anti-VEGF aptamer combining a PEGylated nucleic acid aptamer which binds to and antagonises VEGF. It is approved for the treatment of age-related macular degeneration. Aptamers have also been proposed for use in sequestration and release of therapeutic agents such as growth factors. Battig et al. (2014) Biomaterials 35:8040-8048 describes a super-porous hydrogel matrix, which is proposed as a tissue implant, and which comprises a nucleic acid aptamer used to sequester a growth factor and demonstrates that such sequestration (i.e. loading of the aptamer with growth factor) can be accomplished without the use of harsh conditions, which could compromise the activity of the growth factor. The release rate of the growth factor can be controlled by engineering the binding affinity of the aptamer, but release is by passive diffusion and does not require the presence of cells. The present invention relates to the controlled release of a therapeutic agent, for example a growth factor, from a construct comprising a binding partner, preferably an aptamer, only in the presence of cells, preferably only in the presence of target cells, by making use of cell traction forces to release the therapeutic agent from the binding partner by causing conformational changes in the binding partner.

SUMMARY OF THE INVENTION

In a first aspect of the invention there is provided a molecular complex comprising a therapeutic agent and a controlled release construct, the controlled release construct comprising a primary matrix conjugation site which is linked to an cell adhesive site, via a binding region and optionally via one or more spacer elements, wherein the binding region has a folded configuration in which it is bound to the therapeutic agent, wherein the construct is configured such that when mechanical tension is applied between the primary matrix conjugation site and the cell adhesive site, the binding region adopts a less folded configuration in which bound therapeutic agent is released.

In a second aspect of the invention there is provided a controlled release construct comprising a primary matrix conjugation site which is linked to a cell adhesive site via a binding region and optionally via one or more spacer elements, wherein the binding region has a folded configuration in which it is able to bind to a therapeutic agent, wherein the construct is configured such that when mechanical tension is applied between the primary matrix configuration site and the cell adhesive site, the binding region adopts a less folded configuration which is less able to bind to a therapeutic agent.

In a third aspect of the invention there is provided a pharmaceutical composition comprising a molecular complex according to the first aspect of the invention or a controlled release construct according to the second aspect of the invention and a pharmaceutically acceptable carrier.

In a fourth aspect of the invention there is provided a molecular complex according to the first aspect of the invention or a controlled release construct according to the second aspect of the invention or a pharmaceutical composition according to the third aspect of the invention for use as a medicament.

In a fifth aspect of the invention there is provided a molecular complex according to the first aspect of the invention or a controlled release construct according to the second aspect of the invention or a pharmaceutical composition according to the third aspect of the invention for use as a medicament for aiding tissue regeneration.

In a sixth aspect of the invention there is provided a method of delivery of a therapeutic agent to a subject in need thereof, comprising administering a molecular complex according to the first aspect of the invention or a pharmaceutical composition according to the third aspect of the invention to said subject.

In a seventh aspect of the invention there is provided a method of treating a subject in need of tissue regeneration comprising administering a molecular complex according to the first aspect of the invention, or a controlled release construct according to the second aspect of the invention, or a pharmaceutical composition according to a third aspect of the invention, to said subject.

In an eighth aspect of the invention there is provided a method of making a molecular complex as defined in the first aspect of the invention comprising contacting therapeutic agent with a controlled release construct as defined in the second aspect of the invention.

BRIEF DESCRIPTION OF THE DRAWINGS

FIG. 4 shows a reaction schematic of a collagen gel functionalisation strategy. Such gels may be used in conjunction with constructs of the invention.

FIG. 6 illustrates an experiment used to demonstrate that constructs according to the invention can be conjugated onto collagen gel scaffolds. FIG. 6A illustrates the proposed conjugation reaction using a thiol-DNA construct (AGGGC-CACGTCTATTTAGACTAGAGTCCAGTGGTTC-Thiol (SEQ ID NO: 8) to provide a TrAP construct having the DNA of the thiol-DNA construct linked to collagen matrix (SEQ ID NO:9) duplexed with the ssDNA oligo of SEQ ID NO:6, and FIG. 6B shows fluorescence micrographs which confirm successful conjugation. In the colour originals the top left and top right micrographs show fluorescence in the red channel which is shown as lighter shade in this monochrome reproduction.

FIG. 8 illustrates an experiment demonstrating that a glass surface functionalised with constructs of the invention cause cells to produce focal adhesions and to proliferate more than cells on a control surface.

DEFINITIONS

Aptamer

Figure 1A:
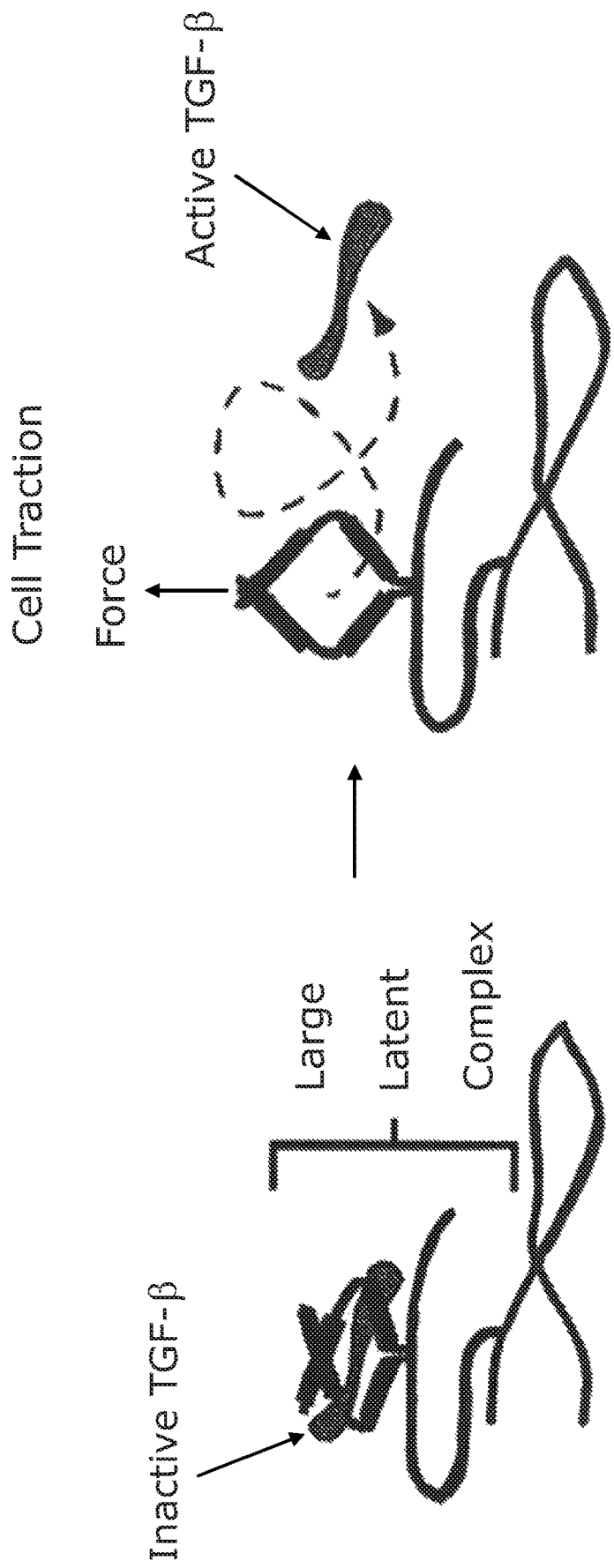
FIG. 1(a) shows the principle at the heart of the invention, that a therapeutic agent (here the growth factor TGF-β is taken as a non-limiting example) can be complexed in an inactive form with a controlled release construct of the invention (described in FIG. 1(a) as "Large Latent Complex"). One end of the construct may be attached to an extracellular substrate or matrix. When the construct has a cell traction force applied to the other end, the controlled release construct changes its configuration such that the therapeutic agent detaches and is released in an active form. The cell traction force is applied to one end of the construct because that end becomes attached to the cell surface and is moved by movement in the cell to which it is attached. It is important to appreciate that cell movement sufficient to result in a cell traction force needed for the present invention to function need not include complete cell migration (although it includes such movement). Even cells which are considered to be not migratory send out processes from their membrane surfaces which local movement will provide sufficient cell tractive forces for the invention to function.

An aptamer is an oligonucleotide, or peptide molecule, or a molecule comprising a mixture thereof, that binds to a specific target molecule. As used herein, it also encompasses analogues and derivatives of oligonucleotides and peptides and also can refer to a part of a larger molecule, such that one or more regions of a molecule in accordance with the invention may comprise an aptamer.

Nucleic Acid

Nucleic acids as described herein include RNA and DNA (and mixtures thereof) and also analogues of naturally-occurring nucleic acids collectively referred to as XNAs and mixtures of any thereof. Nucleic acid analogues include base analogues and backbone analogues. Backbone analogues may be used in some embodiments in order to make the nucleic acid more hydrolysis resistant or to tailor the rate of hydrolysis or other degradation of the molecule to provide a molecule with the desired in vivo half-life.

Pharmaceutically Acceptable Carrier

The invention provides a pharmaceutical composition comprising a molecular complex or a controlled release construct of the invention and a pharmaceutically acceptable carrier. Pharmaceutical compositions of the invention may take the form of any pharmaceutical composition, including those described below.

The pharmaceutical compositions according to the invention include those suitable for oral, parenteral (including subcutaneous, intradermal, intramuscular, intravenous, and intraarticular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The compositions may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

According to certain embodiments, the compositions comprise suitable particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

Compositions also include implantable drug infusion devices used to provide patients with a constant and long term dosage or infusion of a drug or any other therapeutic agent. Essentially such devices may be categorized as either active or passive. A pharmaceutical composition of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as sparingly soluble derivatives, for example, as a sparingly soluble salt.

A therapeutically effective amount of a therapeutic agent may be administered as a single pulse dose, as a bolus dose, or as pulse doses administered over time. Thus, in pulse doses, a bolus administration of an agent is provided, followed by a time period wherein no a compound of the invention is administered to the subject, followed by a second bolus administration. In specific, non-limiting examples, pulse doses of an agent are administered during the course of a day, during the course of a week, or during the course of a month.

In one embodiment, a therapeutically effective amount of the therapeutic agent is administered with a therapeutically effective amount of another agent.

In certain embodiments, the pharmaceutical composition comprises a molecular complex or a controlled release construct of the invention which is conjugated to natural or artificial extracellular matrix component (for example collagen or fibronectin) or a biodegradable polymer, for example as discussed above.

Therapeutic Agent

The invention in all its aspects relates to virtually any therapeutic agent for treating or preventing (but not necessarily curing) a disease, disorder or injury. According to some embodiments of all aspects of the invention the disease, disorder or injury is an injury. Such injuries include bone fractures and full or partial amputations of finger tips, toes, nose tips, or ears. The invention may also relate to treating or preventing injury to skin, for example it may relate to dermal wound repair (such as repair of chronic ulcers, burn and hypertropic scarring). In other embodiments the invention may relate to bone repair (for example treatment of fractures, provision of spinal fusion and the provision of bone grafts). In other embodiments the invention may relate to heart tissue repair (including tissue patch repair following myocardial infarction). In other embodiments the invention may relate to spinal cord repair (for example repair to nerve guides or treatment of non-resectable tumours). In other embodiments the invention may relate to peripheral nerve repair. In certain embodiments the injury may be an injury caused by an ischemic event such as an embolism, thrombus, stroke, myocardial infarction etc. Non-limiting examples of ischemic injuries include ischemic kidney disease and ischemic heart failure.

The therapeutic agent may be a small molecule pharmaceutical or a larger molecule such as a nucleic acid or peptide/protein growth factor. Growth factors contemplated for use with all aspects of the invention include VEGF-A, VEGF-B, VEGF-C, VEGF-D, BMP-2, BMP-4, PDGF-BB, HGF, FGF1, FGF2, FGF7, FGF10, NGF, BDNF, CX3CL1, CXCL12, EGF, Ang1, Ang2, NRG1, NRG2, NRG3, NRG4, TGF-beta, IL-2 and IL-1 PCAF (KAT2B), IGF-1, IGF-2, CNTF, neurotrophin-1, -2, or -3, GDNF. In some embodiments the growth factor may be a cysteine-knot growth factor. In some embodiments the growth factor may be a neurotrophic factor. In some embodiments the therapeutic agent may be one of the specific compounds or classes of compounds recited elsewhere therein.

According to certain embodiments, the invention may be especially applicable for use with a therapeutic agent which, ordinarily, has a very short in vivo half-life and/or a very short in vitro stability ("shelf life") which would ordinarily render it unsuitable for use as a therapeutic or challenging to use as a therapeutic. This is because when part of the molecular complex, the therapeutic agent may be stabilized. For example the invention may relate to a therapeutic agent which has an in vivo half-life of less than a month, a week or a day. Stabilization may allow it to be stored (at 5 or 20 degrees C.) for at least 1 month, 2, months, 6 months or 12 months. Further information on stabilising sensitive therapeutic agents may be found in Jetani et al. (2016) J. Pharm. Sci. Volume 103, Issue 1, Pages 100-106 which is incorporated herein by reference.

DETAILED DESCRIPTION

According to the first aspect of the invention there is provided a molecular complex comprising a therapeutic agent and a controlled release construct, the controlled release construct comprising a primary matrix conjugation site which is linked to an cell adhesive site, via a binding region and optionally via one or more spacer elements, wherein the binding region has a folded configuration in which it is bound to the therapeutic agent, wherein the construct is configured such that when mechanical tension is applied between the primary matrix conjugation site and the cell adhesive site, the binding region adopts a less folded configuration in which bound therapeutic agent is released. A controlled release construct of the invention may also be referred to as a TrAP construct.

Therapeutic Agent

The invention, in all its aspects, is suitable for use with a very wide range of therapeutic agents. The only requirement placed upon the therapeutic agent is that a binding region in accordance with the invention, which is able to bind to the agent, may be produced. Preferably, but not necessarily, that binding has at least a degree of specificity. The therapeutic agent in some embodiments may be a growth factor such as VEGF-A, VEGF-B, VEGF-C, VEGF-D, BMP-2, BMP-4, PDGF-BB, HGF, FGF1, FGF2, FGF7, FGF10, NGF, BDNF, CX3CL1, CXCL12, EGF, Ang1, Ang2, NRG1, NRG2, NRG3, NRG4, TGF-beta, IL-2, IL-10. In particular it may be VEGF-A, VEGF-C, BMP-2, EGF, FGF-2, FGF-10, PDGF-BB or one of the other compounds disclosed herein. Alternatively, it may be another locally acting signalling molecule, for example a member of the gastrin, secretin, motilin, neurotensin, somatostatin, bombesin or serotonin family. In some embodiments it may be a growth factor having a cysteine knot. In other embodiments it may be an immune modulator. In particular preferred embodiments the therapeutic agent may be a ligand for a cell surface receptor. According to some embodiments the therapeutic agent is a protein or peptide having at least 10, at least 20, at least 30, at least 50, at least 70, at least 100, at least 150 amino acid residues.

According to certain alternative embodiments it may be a cytotoxic drug which needs to be targeted to a specific site (for example a tumour site) in order to have therapeutic effect. It is not envisaged to be a problem to produce a binding region which is able to bind to virtually any therapeutic agent.

According to other embodiments, the therapeutic agent may be an anti-allergy agent; an anti-hyposensitisation agent; an anti-cancer agent; an anti-neoplastic agent; an agent for treating anaemia, neutropenia, angina, arrhythmia, haemophilia, heart failure, hyperlipidaemia, hypertension, thromboembolic disorders, ADHD, narcolepsy, dementia, bleeding disorders, anxiety, depression, epilepsy, insomnia, motor neurone disease, Huntingdon's chorea, MS, nausea, Parkinsonism, psychosis; a contraceptive; an anti-infective agent; an agent for treating diabetes, erectile dysfunction, growth disorders, inflammatory disorders, hypogonadism, constipation, diarrhoea, haemorrhoids, IBS, diverticulitis, ulcerative colitis, Crohn's disease, incontinence, renal disorders, urinary tract infections, amoebic infections, bacterial, viral or fungal infection, musculoskeletal disorders, rheumatoid arthritis, obesity, endometriosis, pain, drug and alcohol dependency and asthma; treatments to prevent transplant rejection or to provide immunisation, or to improve fertility.

In many embodiments the binding region will comprise an aptamer. Aptamer technology advantageously permits the generation of aptamers able to bind to an extremely wide range of compounds.

In many embodiments of all aspects of the invention the therapeutic agent is one which needs to be targeted to a specific cellular site in order to have maximum efficacy and/or minimal side effects elsewhere. Non-limiting examples include thrombolytic therapeutic agents which can be targeted to clot sites (for example, tissue plasminogen activator t-PA, alteplase, reteplase), tenecteplase, anistreplase, streptokinase or urokinase) anti-cancer agents which can be targeted to tumour sites and growth factors (for example those recited elsewhere herein) which can be targeted to sites of tissue regeneration.

Subjects for Treatment

According to all aspects of the invention, the subject to be treated is an animal, for example a mammal. Most preferably the subject is human, for example a man or woman, adult, child or infant. However, the invention also relates to non-human animals, including those of agricultural importance (including cattle, sheep, goats, pigs, poultry), sporting animals (including horses, camels and racing dogs and birds) experimental animals (including rodents—mice, rats and rabbits, zebra fish, fruit flies, nematodes, amphibians, dogs, cats and primates) companion animals (including domestic dogs and cats) and animals of conservation concern (including big cats, elephants, monkeys, pandas etc.)

Controlled Release Constructs

The controlled release construct in accordance with all aspects of the invention may be a single molecule or it may consist of several molecules held together with intra-molecular forces.

Essentially, it comprises three regions; a primary matrix conjugation site and a cell adhesive site linked together via a binding region and, optionally, via one or more spacer elements.

FIG. 2 shows diagrammatically various non-limiting example configurations of the controlled release construct.

Figure 2A:
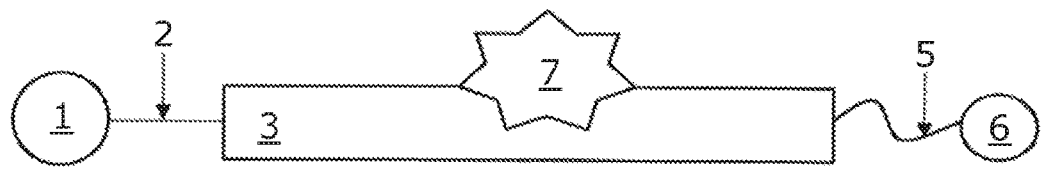
FIG. 2 illustrates diagrammatically several example arrangements for controlled release constructs of the invention.

FIG. 2(a) shows diagrammatically one arrangement in accordance with the invention. Here a controlled release construct of the invention comprises a primary matrix conjugation site (1), linked to a cell adhesive site (6) via a binding region (3) and via spacers (2) and (5). The binding region (3) has a folded configuration which allows a therapeutic agent (7) to bind it, although, for simplicity, that folding is not shown in FIG. 2(a).

Figure 2B:
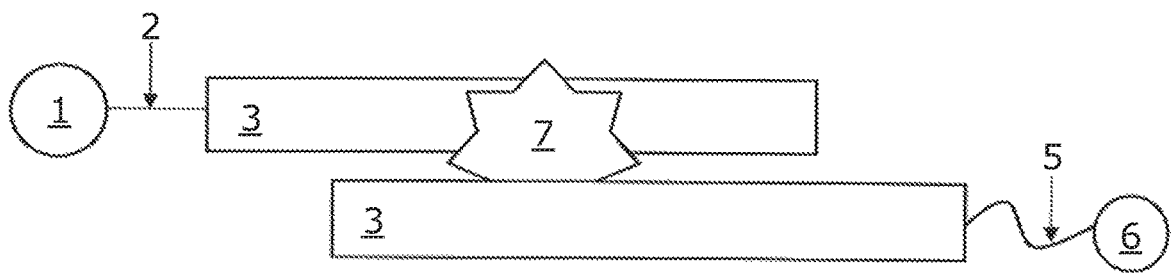

FIG. 2(b) shows an alternative arrangement wherein the binding region (3) consists of two separate molecules non-covalently associated with each other and, although for the sake of simplicity not shown in FIG. 2(b), both parts of the binding region will be folded so as to form a binding region for therapeutic agent (7).

Figure 2C:
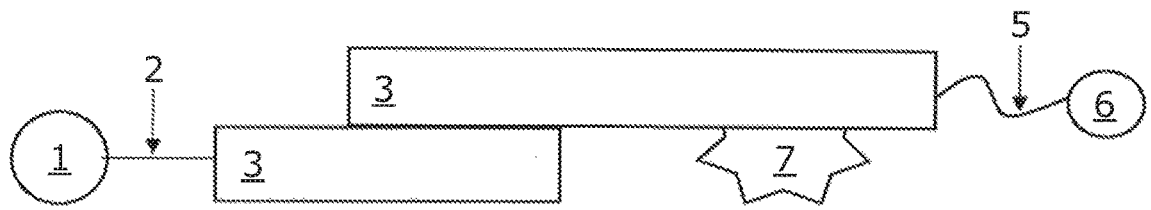

FIG. 2(c) shows a similar arrangement wherein the binding region (3) again consists of two parts non-covalently associated with each other, but where the therapeutic agent (7) associates with a part of the binding region which is formed from only one part, which again would be suitable folded, although for simplicity folding is not shown in FIG. 2(c).

Figure 2D:
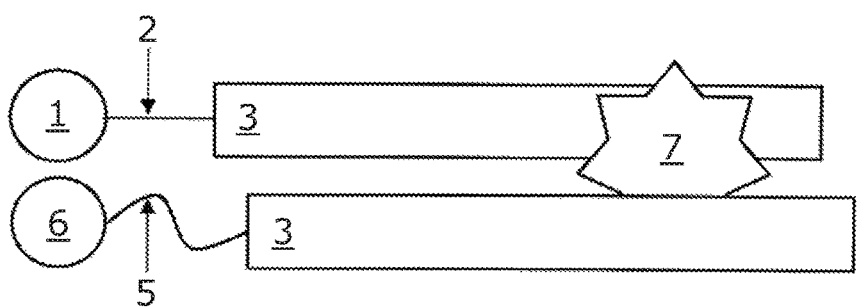

FIG. 2(d) is similar to FIG. 2(b) but the primary matrix conjugation site and the cell adhesive site are in close proximity for the sake of illustrating that they need not be placed at opposite ends of the construct.

FIGS. 2(b), 2(c) and 2(d), in certain embodiments, will represent controlled release constructs of the invention wherein the binding region (3) comprises two nucleic acid claims non-covalently associated (for example by base-pair annealing) and FIGS. 2(b) and 2(d), in certain embodiments, will represent constructs wherein the therapeutic agent will be a nucleic acid intercalating drug such as an anti-cancer agent like doxorubicin and the unfolding of the nucleic acid binding region will include a reduction in double-stranded regions and a consequent release of therapeutic agent.

Matrix Conjugation Sites

Figure 1B:
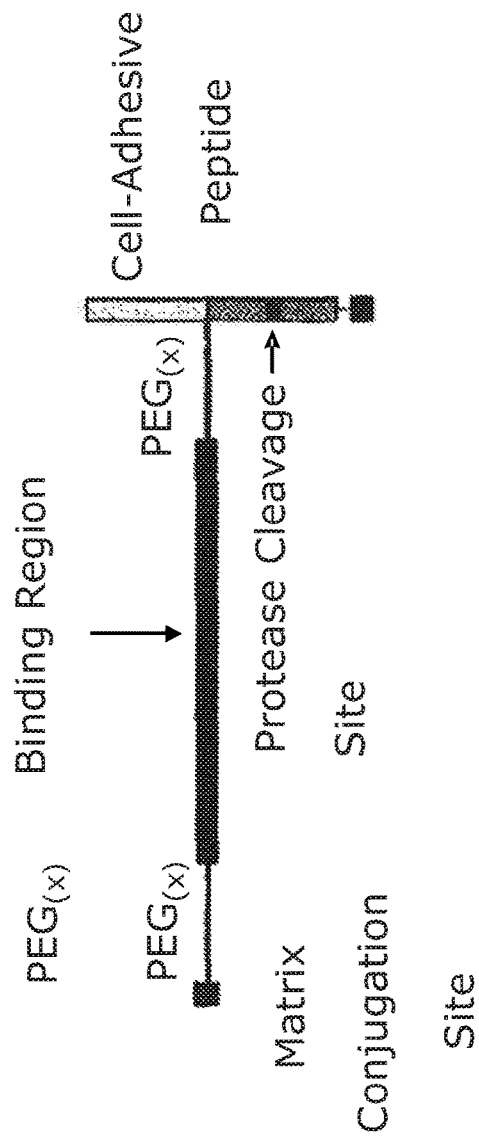
FIG. 1(b) shows a schematic structure of a construct according to certain embodiments of the invention discussed herein in the first panel and, in the lower panel, a controlled release construct according to certain embodiments of the invention which comprises a second matrix conjugation site and a protease cleavage site.
Figure 1B:
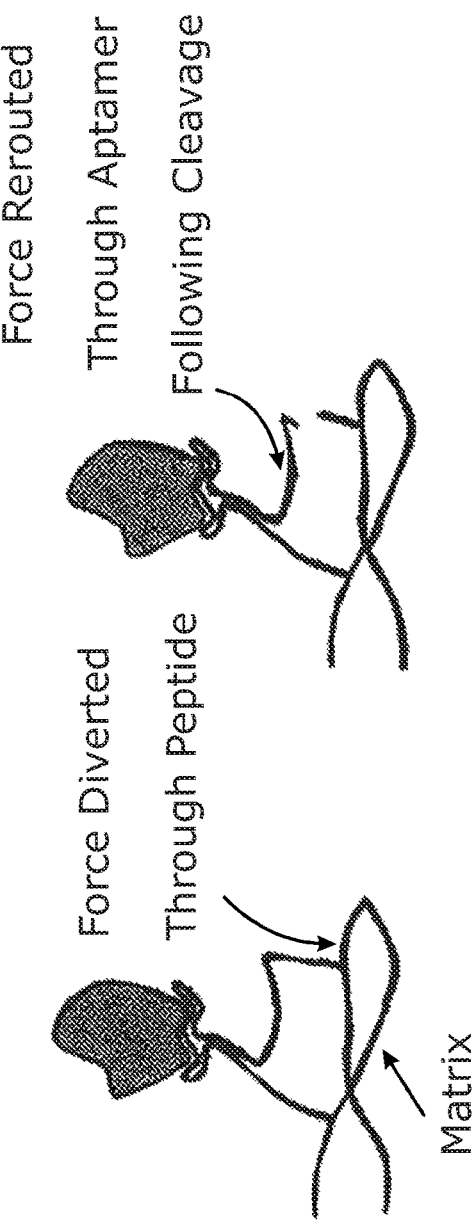
Figure 1C:
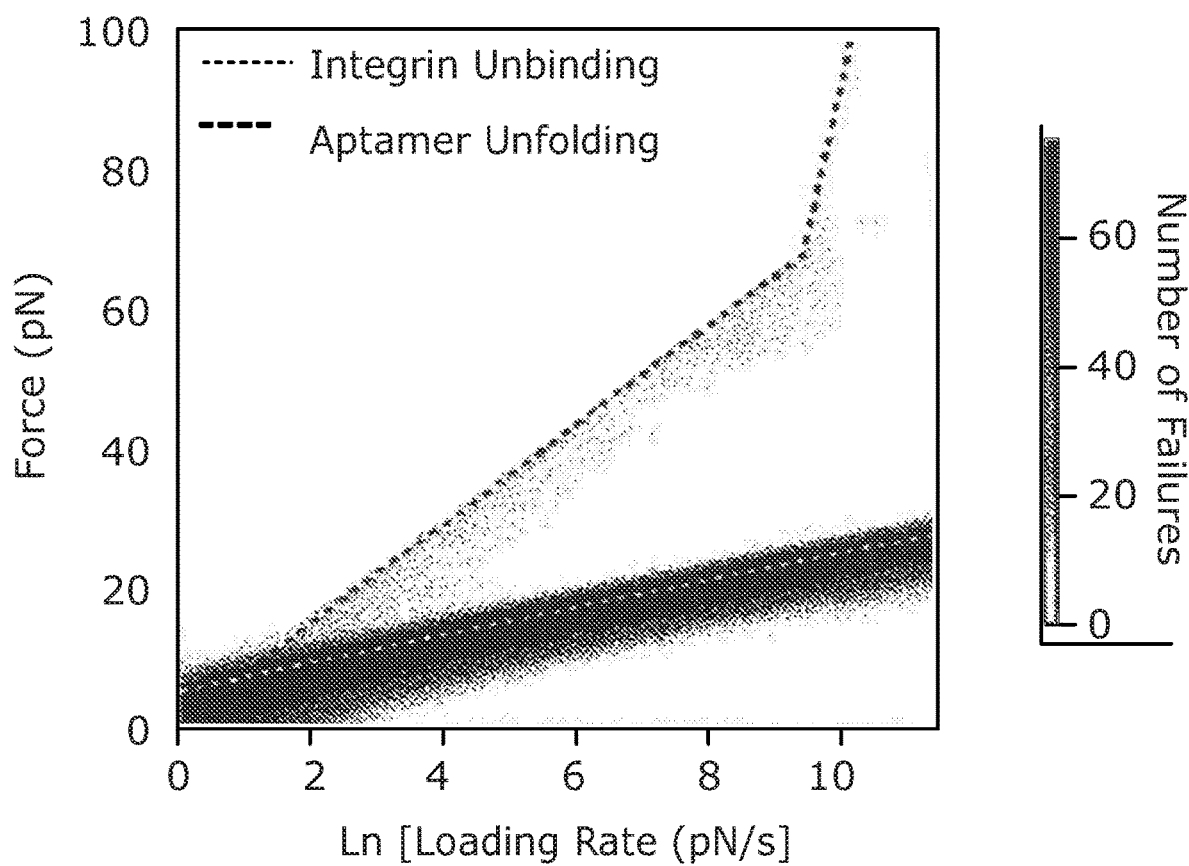
FIG. 1(c) shows a Monte Carlo simulation demonstrating that an aptamer binding site such as that proposed for use with certain embodiments of the invention will unfold and release the therapeutic agent prior to an integrin cell adhesive site unbinding from an integrin.

All controlled release constructs in accordance with the invention comprise at least one matrix conjugation site referred to as the primary matrix conjugation site. Optionally, the construct may comprise a further matrix conjugation site, referred to as the secondary matrix conjugation site. The primary matrix conjugation site is linked to the cell adhesive site via the binding region, such that any increase in distance between the primary matrix conjugation site and the cell adhesive site results in the binding region being subjected to mechanical tension. This is shown diagrammatically in one arrangement in FIG. 1(b), wherein the black square labelled "matrix conjugation site" is the primary matrix conjugation site and the second, unlabeled, black square is the secondary matrix conjugation site. If present, the secondary matrix conjugation site is linked to the cell adhesive site, not via the binding region, so that any mechanical tension between the secondary matrix conjugation site and the cell adhesive site is not experienced by the binding region and wherein, when both the primary and secondary matrix conjugation sites are joined to a component of the extracellular matrix, tension force between the matrix and the cell adhesive site is not routed via the binding region. In such an arrangement a breakage in the controlled release construct between the secondary matrix conjugation site and the cell adhesive site results in tension force between the matrix and the cell adhesive site being routed through the binding region of the construct. The construct may be arranged so that there is provided a cleavage site between the secondary matrix conjugation site and the cell adhesive site. This may, for example, be a nuclease or a protease cleavage site as labelled in FIG. 1(b). By providing a nuclease or protease cleavage site, it can be arranged that the binding region of the construct is only subjected to a tension force in or subsequent to the presence of a nuclease or protease which is able to cleave to the construct at the cleavage site. Such an arrangement can serve as a molecular AND-gate and increase the spatial and temporal specificity of the release of the therapeutic agent from the construct such that the therapeutic agent is released when the binding region is subjected to a tension force and that this only happens when the cell adhesive site adheres to a cell and is subjected to a cellular traction force AND when the cleavage site is cleaved so that that force is routed via the binding region. The cell adhesive site can be made more or less specific for a specific cell type and the cleavage site can be made more or less specific for a specific cleavage enzyme.

If the degree of specificity of each of those things is incomplete, a greater degree of overall specificity is to be found in requiring both partly-specific conditions to be met. As an illustrative example, a molecular complex according to the invention for use in delivering an anti-cancer therapeutic agent may be provided wherein the cell adhesive site has partial specificity for the tumour cell type. Full tumour cell specificity may be difficult to achieve, but the construct according to the invention may further comprise a secondary matrix conjugation site and a cleavage site as described above, wherein the cleavage site is specific for a cleavage enzyme, for example a matrix metalloprotease (MMP), which although not exclusively found in tumour sites, but is significantly upregulated in them.

The construct may be arranged so that the therapeutic agent is delivered in substantial amounts only when both the cell adhesive site is bound to a surface molecule found on the target cell type AND where the construct is exposed to a protease which is upregulated at tumour sites. By means of such a molecular AND-gate, increased specificity of the delivery of the therapeutic agent is achieved and thereby efficacy increased and side-effects reduced.

According to all aspects of the invention, the term "matrix conjugation site" encompasses moieties of the construct which are adapted to be conjugated to the matrix both before and also after conjugation. The term "matrix" in this context refers to the naturally occurring extracellular matrix (ECM) or a component thereof (such as collagen or fibronectin, for example) and also ECM components, or derivatives or analogues thereof, which have been artificially provided, for example implantable collagen sponges, injectable fillers or implantable nerve guidance conduits. The term also encompasses any other extracellular substance, both natural and synthetic, and specifically includes an extracellular thrombus, laboratory plastic ware (and coatings thereof) and any ex-vivo or implantable medical device or part thereof. The matrix binding site may structurally be a chemically reactive moiety or it may be a protein or other molecule adapted to bind to the matrix. According to certain embodiments matrix binding is specific. According to other embodiments it is non-specific. For some embodiments the matrix conjugation site may be a one member of a known conjugation pair. For example a maleimide/thiol pair, wherein one member of that pair is the matrix conjugation site and the other member of that pair is provided as a moiety on the matrix. In some embodiments the matrix may be made of Dextran, poly glycerol sebacate, poly lactic co-glycolic acid, collagen, a collagen derivative, fibronectin or a fibronectin derivative or a mixture of any one or more thereof. According certain optional embodiments the matrix may be engineered to fully or partially degrade over time (for example over a day, week, month, year or decade) in the body. To control the rate of degradation, a matrix may contain specific recognition sites for degradative enzymes. For example both natural and artificial matrices may contain the KCGPQG↓IWGQCK peptide sequence motif which renders it susceptible to MMP degradation.

Cell Adhesive Site

The cell adhesive site of the construct according to all aspects of the invention is a region of the construct able to adhere to the surface of a cell. According to certain embodiments this adherence is cell-type specific. According to other embodiments this adherence is cell-type non-specific. The cell adhesive site may be a peptide, protein or other binding moiety. According to some embodiments it comprises an antibody or derivative thereof. According to other embodiments it is a peptide able to adhere to a receptor present on the surface of either all cells or specific cells. For certain embodiments, the cell adhesive site may comprise an integrin binding moiety such as an RGD peptide. According to other embodiments, the cell adhesive site may be an antibody, derivative thereof, or protein receptor for a cell surface marker which is present on cells to be targeted by the therapeutic agent. For example, if the cells to be targeted are multiple myeloma cells, a cell adhesive site may be provided which binds preferentially (even if not exclusively) to multiple myeloma cells, for example the cell adhesive site may comprise an anti CD138 or CD319 antibody or derivative thereof, or a binding partner of CD138 or CD319, such as CXCL12, or fibronectin, or a derivative, or part thereof.

In certain embodiments, the matrix binding site(s) of the controlled release construct may be specific for the body site to which the therapeutic agent is to be targeted. In such cases, the cell adhesive site may not need to be specific for a particular cell type and a cell adhesive site is chosen simply for its ability to bind well to cells in general. For example, if the matrix binding site is provided to bind specifically to a thrombus, the cell adhesive site may simply be designed to bind to a surface entity which is ubiquitous to all cells or common to many cell types so that it may be assumed that there will be sufficient cells in the vicinity of the thrombus to provide a cell traction force to ensure therapeutic agent delivery without a specific cell type needing to be present.

In other embodiments the cell adhesive site and the matrix binding site(s) may both be at least somewhat specific for the tissue site in need of the therapeutic agent. By such an arrangement, superior specificity of delivery of the therapeutic agent may be achieved.

In other embodiments, the controlled release constructs according to the invention comprise an artificially produced matrix to which the matrix binding site(s) has been conjugated. That is to say that the matrix binding site and the artificially produced matrix are already conjugated as part of the manufacturing process of the controlled release construct.

Binding Region

According to all aspects of the invention, the binding region of the controlled release construct meets the criterion of having a first configuration and a second configuration. The first configuration is one in which the binding region is at least partially folded into a tertiary structure which provides for it to bind relatively strongly to the therapeutic agent. The second position is one in which the binding region is less folded and in this less folded configuration is less able to bind to the therapeutic agent, such that it may be released and effectively "delivered" to carry out its therapeutic effect. According to some embodiments, the more folded configuration comprises a greater proportion of double stranded nucleic acid regions than the less folded configuration. In certain embodiments, the more folded configuration has one or more nucleic acid hairpins which are lost or reduced in the less folded configuration. The binding region transitions from the first to the second position when it is subjected to mechanical tension. Most simply, the binding region has an essentially linear primary molecular structure, wherein this essentially linear primary molecular structure undergoes, preferably spontaneously, higher order folding. When the "ends" of the linear structure are pulled apart, this at least partly undoes the higher order folded structure. The binding region may comprise a nucleic acid, peptide or other molecular structure. In certain embodiments, it is a nucleic acid or derivative/analogue thereof and in certain embodiments it is an aptamer, such as a nucleic acid (or derivative/analogue thereof) aptamer.

Nucleic acid aptamers are especially advantageous because they can be easily generated to a very wide range of binding partners and because they are able to be folded easily by an appropriate heating/melting and cooling/annealing process and because they may be subsequently loaded with the binding partners under relatively gentle non-denaturing conditions.

However, in certain embodiments, the binding region may comprise a nucleic acid (or derivative/analogue thereof) without necessarily meeting the definition of an aptamer. In certain embodiments the binding region may comprise nucleic acid (or a derivative/analogue thereof) having a significant degree of base pair annealing (for example by providing a hairpin structure of double stranded nucleic acid). This annealed region of the binding region may be suitable for binding a nucleic acid intercalating therapeutic agent, for example doxorubicin. When the binding region is subjected to mechanical tension the base pairs will come apart and the therapeutic agent, being a compound that selectively binds to double stranded regions of nucleic acid, will be released.

In other embodiments, the binding region comprises a nucleic acid (or derivative/analogue thereof) aptamer. The binding site of an aptamer is dependent on a higher-order folding of its structure so that it will be able to bind to the therapeutic agent when the binding region is in its folded configuration, but not (or to a lesser degree) when the folding is lost due to the aptamer being subjected to a tension force.

It will be within the capability of a person skilled in the art to produce a nucleic acid aptamer for virtually any ligand (and especially any peptide or protein ligand, for example one having a residue length limit as given above) using the 25 year old SELEX (Systematic evolution of ligands by exponential enrichment) technique and developments thereof. See Spill et al (2016) PNAS 113 (43): 12076-12081 and references therein (which are hereby incorporated by reference) for further details of the SELEX technique. It is also noted that the generation of aptamers has become so routine that it is offered on a fixed price contract basis by a under of organisations such as BasePairBio (Pearland, Tex.), Ray Biotech (Norcross, Ga., USA), Somalogic (Boulder, Colo.), who offer a system called SOMAmer (T.M) and Trilink Biotechnology (San Diego, Calif.). A nucleic acid aptamer for use in relation to the invention may comprise naturally occurring nucleotide residue or non-naturally occurring residues, or derivatives of residues, or a mixture of any thereof.

Spacers

The spacers or "spacer elements" of the binding construct in all aspects of the invention are entirely optional, but are preferably included when needed to allow any of the other parts of the construct (the matrix conjugation site, the binding region and the cell adhesive site) to fully function without interference with each other. Any suitable spacer may be used, including an alkyl chain or polyethylene glycol (PEG) chain of an appropriate length. Alterative, non-limiting examples of spacer moieties include peptides, nucleic acids, polysaccharides, and synthetic polymers, or analogues and derivatives of any thereof.

Spacers may be especially useful wherein other parts of the controlled release construct (the matrix conjugation site, the binding region and the cell adhesive site) are bulky and need to be spaced apart from each other to allow correct folding and/or function without interference.

Constructs of the Invention

According to a second aspect of the invention there is provided a controlled release construct comprising a primary matrix conjugation site which is linked to a cell adhesive site via a binding region and optionally one or more spacer elements, wherein the binding region has a folded configuration in which it is able to bind to a therapeutic agent, wherein the construct is configured such that when mechanical tension is applied between the primary matrix conjugation site and the cell adhesive site, the binding region adopts a less folded configuration which is less able to bind to a therapeutic agent. Constructs of the invention may also be referred to herein as TrAPs.

Many optional features of the controlled release construct have already been described above in the discussion of the first aspect of the invention and they apply equally to the second aspect of the invention and vice versa.

A controlled release construct of the invention may be provided with or without an extracellular matrix. For example, it may be supplied with a matrix conjugation site or sites which are not yet conjugated to a matrix but will be able to do so either in vivo following administration to a subject or as part of a later in vitro manufacturing step. The invention in this aspect also provides a controlled release construct wherein the matrix conjugation site is pre-conjugated to an artificial matrix (albeit one which may be made of a natural material) such as a collagen sponge or a synthetic biodegradable polymer, such as polyglycolide, polyactide, poly(ε-caprolactone), poly(dioxanone), poly(lactide-co-glycolide), or poly(orthoester). The matrix may be formed into a sponge, gel or cellular scaffold, or a stent, or as a coating on a medical device. The invention also encompasses in its first aspect, a molecular complex comprising such a controlled release construct.

A controlled release construct according to the second aspect of the invention may be useful as an intermediate in manufacturing a molecular complex of the first aspect of the invention by allowing a therapeutic agent to bind to the binding region. In some embodiments, controlled release constructs according to the second aspect of the invention may, of themselves, be therapeutically useful, even if no therapeutic agent is included in them. Such "empty" controlled release constructs may be useful when correctly localised in the body in scavenging naturally occurring growth factors or other natural signalling molecules present at low levels in the extracellular milieu and releasing them in the presence of a target cell type, thereby producing higher local concentrations in the vicinity of the target cells.

Accordingly, such "empty" constructs according to the invention may be especially preferred which are able to bind to a therapeutic agent which is a growth factor, or a signalling molecule naturally present in the body and where optionally the cell adhesive site is specific for binding to cells that are in need of the therapeutic agent.

Fine Tuning of Constructs

The technology of aptamers and related molecules allows the properties of controlled release constructs in accordance with the invention to be fine-tuned. For example, nucleic acids and related molecules can be made with different bases in order to control the degree of base-pairing and the melting temperature of double stranded regions. The in vivo half-life of nucleic acid and peptide parts of the construct can be fine-tuned by introducing the required proportion of derivatized residues so as to tailor-make a construct having the desired susceptibility to degradation (for example by nucleases/proteases). Aptamer selection technology allows binding regions to be engineered with relative ease and following well-understood methods of mutation and selection, which have the desired degree of specificity versus cross-reactivity and with the desired degree of binding affinity.

The different parts of a controlled release construct according to the invention may each be optimised separately and then be brought together into a single construct having optimised properties in each of its parts.

Pharmaceutical Compositions

The invention provides, in its third aspect, a pharmaceutical composition comprising a molecular complex according to the first aspect of the invention or a controlled release construct according to the second aspect of the invention and a pharmaceutically acceptable carrier. Preferred features of the molecular complex and the controlled release construct may be as described herein with reference to the first and second aspects of the invention. The pharmaceutical composition can optionally take any form as described herein as can the pharmaceutically acceptable carrier.

According to certain embodiments, the composition is suitable for injection or infusion, for example in an aqueous solution in an infusion bag or syringe suitable for intravenous, intramuscular, intraocular or subcutaneous administration.

In other embodiments, the composition may be suitable for administration to a mucous membrane, for example to a gut membrane, an intranasal membrane, a buccal membrane, or other mucous membrane. Other suitable routes of administration may be topical, transdermal, sublingual, sublabral (gingival), enteral, gastric, epidural, intracerebral, intracerebroventricular, extra amniotic, intraarticular, intracardiac, intracavernous, intradermal, intralesional, intraosseous, intraperitoneal, intrathecal, intrauterine, intravaginal, intravesical (urinary bladder), inhalational, rectally and intraarterial (especially suitable for delivery of thrombolytic agents).

According to certain embodiments wherein the molecular complex of the invention or the controlled release construct of the invention comprises a matrix, the pharmaceutical composition may include substances for keeping the matrix properly hydrated and sterile. For example, a buffer and sealed container may also be supplied in a device suitable for introduction to the body. For example, wherein the controlled release construct comprises a synthetic sponge or other implantable matrix, the pharmaceutical composition of which it is a part may further comprise a buffer solution to keep the matrix hydrated and may be supplied sterile in a sealed container. Where the controlled release construct comprises an injectable gel into which the matrix conjugation site is conjugated, the pharmaceutical composition of which it is a part may be supplied in a pre-loaded syringe for injection. According to certain embodiments the controlled release construct may comprise a nerve guidance conduit or a natural or artificial gel material (for example one of the gel materials described herein). In such embodiments the controlled release construct may be suitable for the controlled release of a neurotropic factor (for example one of the growth factors listed herein). It is also to be understood that the invention encompasses molecular complexes according to the first aspect of the invention comprise a matrix, for example a matrix described above in reference to a controlled release construct according to the second aspect of the invention.

Medical Methods and Uses

The fourth to seventh aspects of the invention relate to using a complex of the invention for treating a disease, disorder, or injury, or in the provision of a medicament for treating a disease, disorder or injury. Especially amenable diseases, disorders and injuries to be treated in accordance with the invention include large and/or non-healing dermal wounds (e.g. burns, venous ulcers, pressure ulcers, hypertrophic scarring and diabetic ulcers), disorders amenable to treatment by bone grafts (e.g. spinal fusion for degenerative disc disease or scoliosis), bone injury (ie fractures) heart disorder amenable to treatment by cardiac patches (e.g. myocardial infarctions), non-resectable tumours and spinal cord damage.

Methods of delivery of a therapeutic agent to a subject in need thereof and methods of treating a subject in accordance with the invention comprise a step of administering a molecular complex or controlled release construct of the invention. They may comprise steps of surgery (i.e. surgical implantation) administration by injection into an appropriate body site or administration by any of the other administration routes described herein.

Methods of Making a Molecular Complex

According to the eighth aspect of the invention there is provided a method of making a molecular complex defined according to the first aspect of the invention comprising contacting a therapeutic agent with a controlled release construct as defined according to the second aspect of the invention. The therapeutic agent may preferably be as defined elsewhere herein and the contacting step preferably comprising bringing the therapeutic agent and the controlled release construct together in a solution (for example a compatible buffered saline solution or other aqueous solution) for sufficient time for the therapeutic agent to bind to the controlled release construct. Typically a few hours will be sufficient for the binding to take place (for example 1 to 6 hours, 1 to 24 hours, 2 to 6 hours, 1 to 2 hours). Typically, the therapeutic agent and the controlled release constructs are brought together at approximately room temperature (for example at a temperature or between 1 to 35, 1 to 30, 5 to 25, 10 to 25, or 15 to 25 degrees Celsius). Such a "gentle" loading process minimises possible damage to the therapeutic agent.

EXAMPLES

Example 1

Production of a Controlled Release Construct

An aptamer previously shown to bind VEGF with a $K_D$ of 0.2 nM, and previously described as SEQ ID NO: 42 in U.S. Pat. No. 7,153,948 B2, which is therein incorporated by reference was used as the binding region of the controlled release construct. It was synthesized using a solid phase synthesis and modified to contain an amine group on its 5' end and a maleimide group on its 3' end. More specifically, the 5' end was post-synthetically modified with amino-PEG using azidohexanoic acid, followed by a reaction with a DBCO-amine spacer. The 3' end was post-synthetically modified with an amino (C7) spacer with maleimide [PEG] 8.

Next, the 3' end was coupled to a cell adhesive site, or in the control construct a site not showing cell adhesive properties. In both cases the site was a peptide sequence and a sequence of either a biologically active peptide or, for the control, its scrambled counterpart was used. The peptide sequences used were cyclo(Arg-Gly-Asp-D-Phe-Cys) (cyclo (SEQ ID NO: 1) and cyclo(Arg-Ala-Asp-D-Phe-Cy (cyclo(SEQ ID NO: 2), respectively. The Arg-Gly-Asp (RGD) is a biologically active (integrin binding) part of the first peptide and Cys contains a thiol which reacts with maleimide with high efficiency. The coupling between peptides and the aptamer was achieved through a thiol-maleimide reaction following reduction of disulfide bonds between cysteines using TCEP.

—Conjugation of the Controlled Release Construct to a Matrix

The controlled release construct described above comprises an amino-modified 5' nucleic acid moiety which constitutes a primary matric conjugation site. In order to conjugate the controlled release construct to a matrix they were coupled to polyacrylamide-functionalized coverslips through their amino-modified 5'end.

The functionalization was achieved as follows. First, 5-mm coverslips were coated with polyacrylamide hydrogel (8% acrylamide, 0.48% bis-acrylamide) using a protocol by Tse & Engler (DOI:10.1002/0471143030.cb1016s47, herein incorporated by reference). The polyacrylamide surface was activated using sulfo-SANPAH exposed to 365-nm UV light for 10 minutes.

Subsequently the controlled release constructs described above were added to the polyacrylamide gel covered coverslips at 100 ng/ml in 50 mM HEPES and incubated overnight at 37° C. This mixture additionally contained a Gly-Arg-Gly-Asp-Ser ("RGD containing", SEQ ID NO: 3) sequence at 100 µg/ml, because it has been previously established that polyacrylamide gels without cell adhesive peptides do not promote cell adhesion and survival. The next day, the coverslips were rinsed thoroughly with PBS to remove any unbound chemicals. Next, the matrix-conjugated controlled release constructs were loaded with VEGF by incubating them in a VEGF containing PBS solution (1000 ng/ml) for 2 hours. The same incubation regimen was applied to control coverslips to which the controlled release construct had not been conjugated. The unbound VEGF was then removed by aspirating the incubation medium and by rinsing the coverslips with PBS.

—Cell Proliferation Assay

Finally, the coverslips were seeded with human microvasculature endothelial cells 1 (HMEC-1) that have previously been shown to proliferate in a VEGF concentration dependent manner.

A cell proliferation assay was carried out in a 96-well plate with a seeding density of 10 000 cells/well and 7 repeats per condition. Cell proliferation was quantified fluorometrically on a plate reader after 24 hours using the PrestoBlue™ assay.

RESULTS AND CONCLUSION

Figure 3:
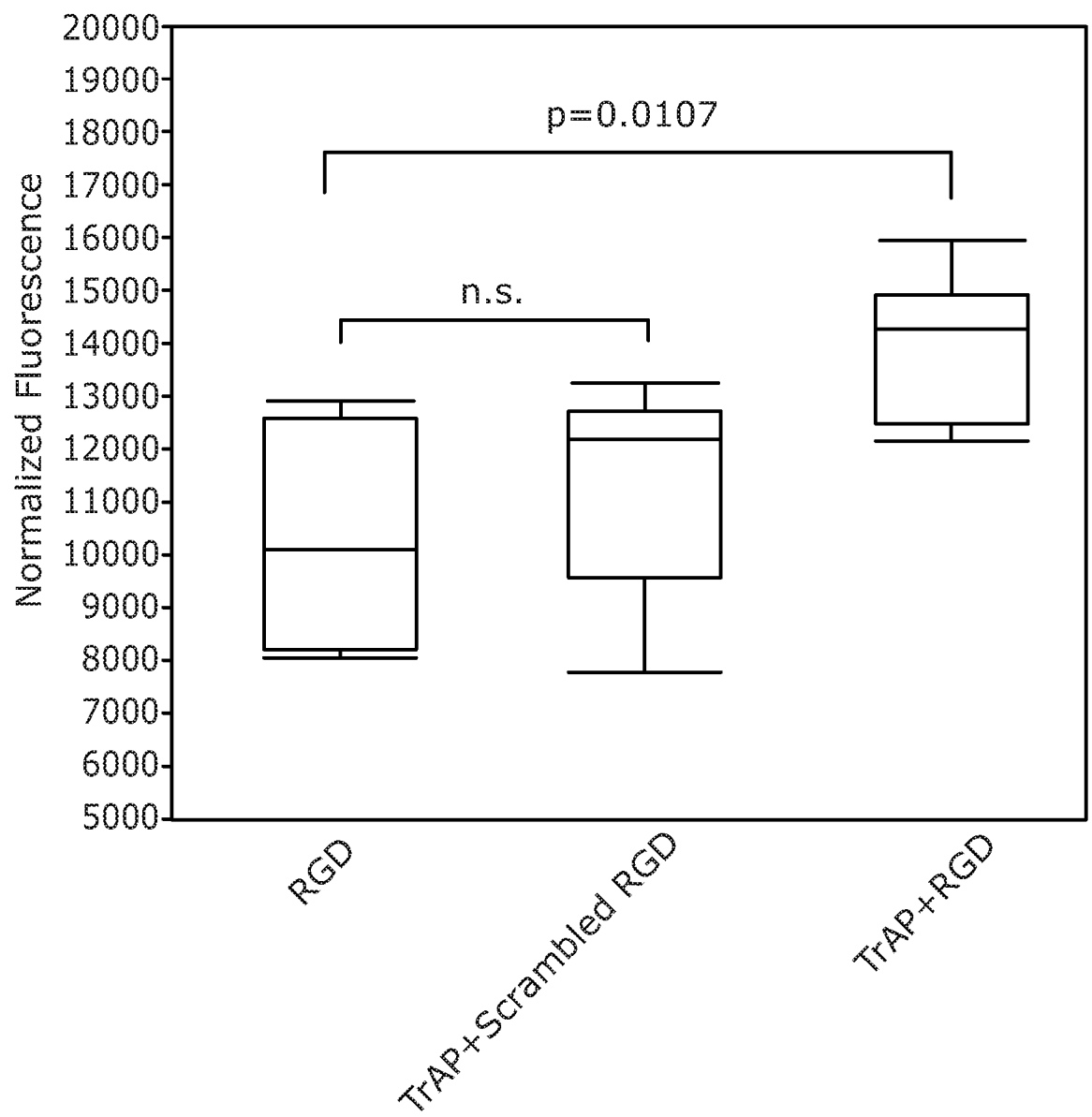
FIG. 3 shows results from the experiment as described in Example 1.

The results are presented in FIG. 3. The first column ("RGD") shows the level of proliferation when non controlled release construct is used. The second column shows the level of proliferation when a controlled release construct loaded with VEGF is used but when the controlled release construct is non-functional because the cell adhesive site is disabled by having its RGD sequence scrambled. The final column shows a significantly higher level of proliferation where a functional controlled release construct which is loaded with VEGF is used. From this higher level of proliferation one can infer that the VEGF growth factor is being released to the cells at a higher level than it is when the controlled release construct is functionally disabled.

Figure 10B:
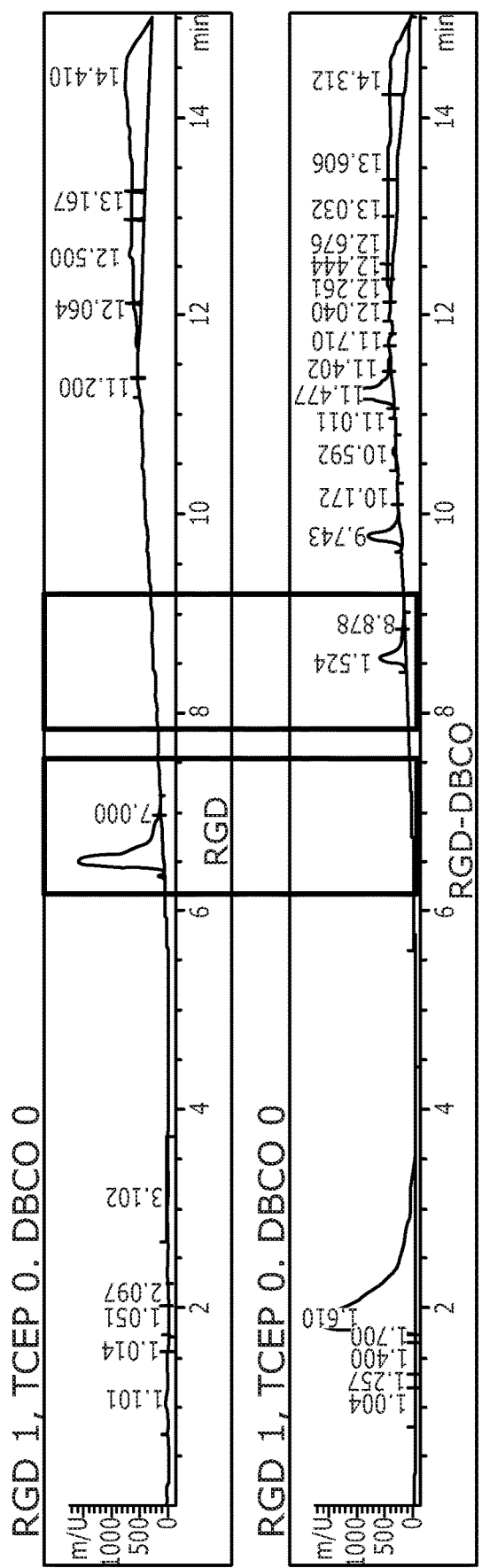
FIG. 10 illustrates the fabrication of TrAP constructs of the invention (FIG. 10 (i), (ii) and (ii)) and their characterisation by HPLC (FIG. 10. (a), (b), (c), (d).
Figure 10C:
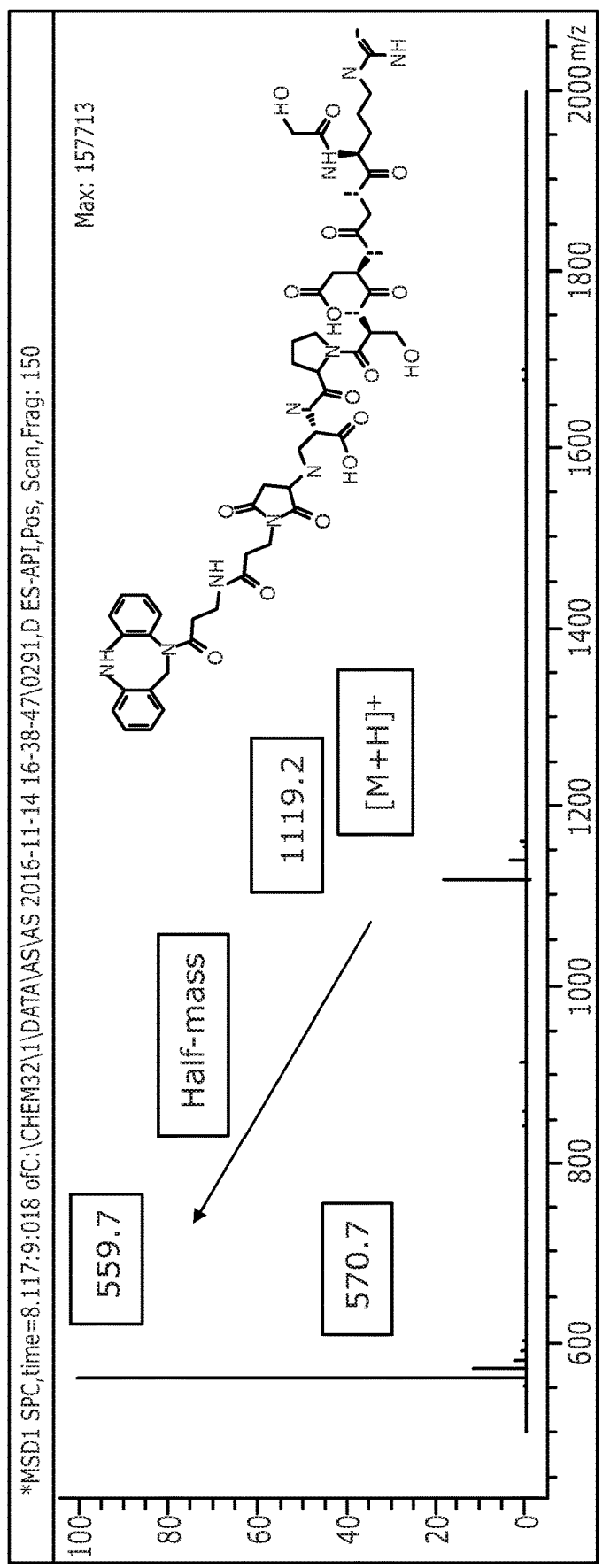
Figure 10D:
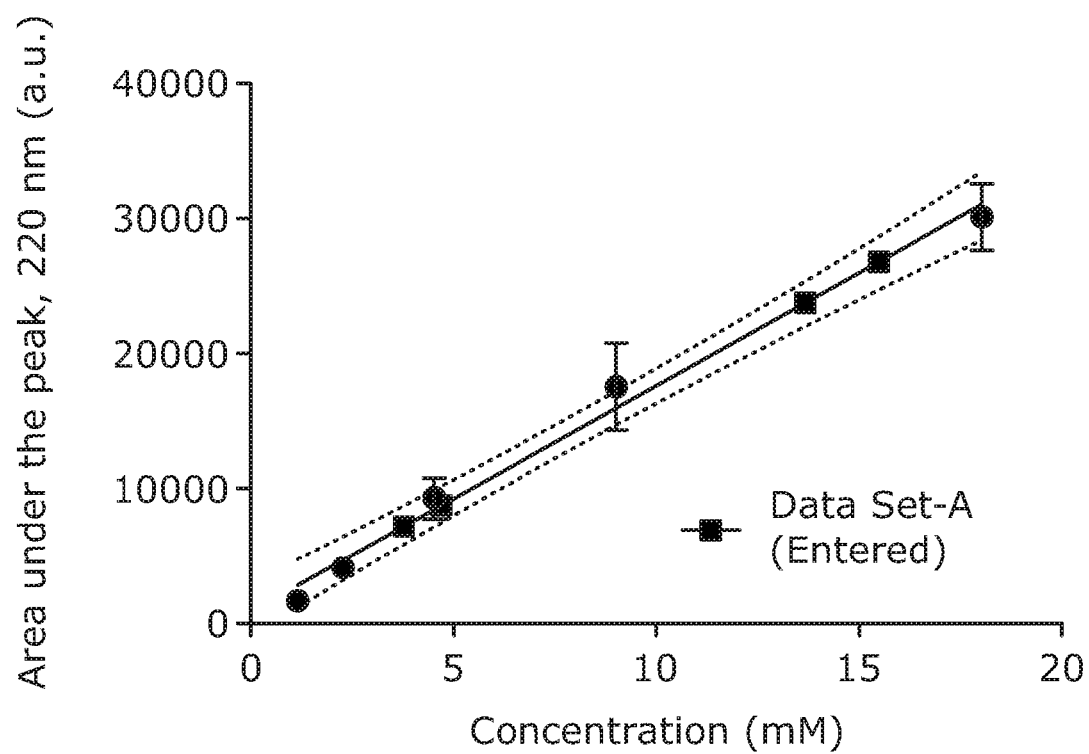

FIG. 10 provides further information regarding the synthesis of the TrAP construct. FIG. 10 (i) shows a peptide cell adhesion site (for example a peptide having the RGD sequence or a scrambled sequence control thereof) and a terminal Cys residue which was commercially purchased. They were run through a TCEP containing reducing gel so as to reduce the thiol group. The peptide was then reacted with a maleimide-DBCO heterofunctional linker to yield a peptide-DBCO conjugate. FIG. 10 (ii) illustrates a ssDNA aptamer which is synthesised commercially using standard resin chemistry to have a S—S group on one end and an azide group on the other end. FIG. 10 (iii) illustrates that the functionalised peptide and the DNA aptamer can be reacted together using a DBCO-azide click reaction to form a construct of the invention. FIG. 10 also provides data relating to the characterisation of the TrAP construct described above. FIG. 10 (a) shows the calculated molecular weight of the species illustrated in FIG. 10 (i) to (iii). FIG. 10 (b) is a HPLC trace (LC-MS) showing that the GRGDSP (SEQ ID NO: 4) peptide peak caused by the cell adhesion site peptide disappeared and was replaced by the peptide-DBCO conjugate peak on completion of the reaction shown in FIG. 10 (i) to (iii). Two other peaks correspond to TCEP-DBCO and unreacted maleimide-DBCO linker. FIGS. 10 (c) and (d) show respectively the IE spectrum of the GRGDSP-DBCO species from the LC-MS device and the calibration curve for this product.

Figures 11A, 11B:
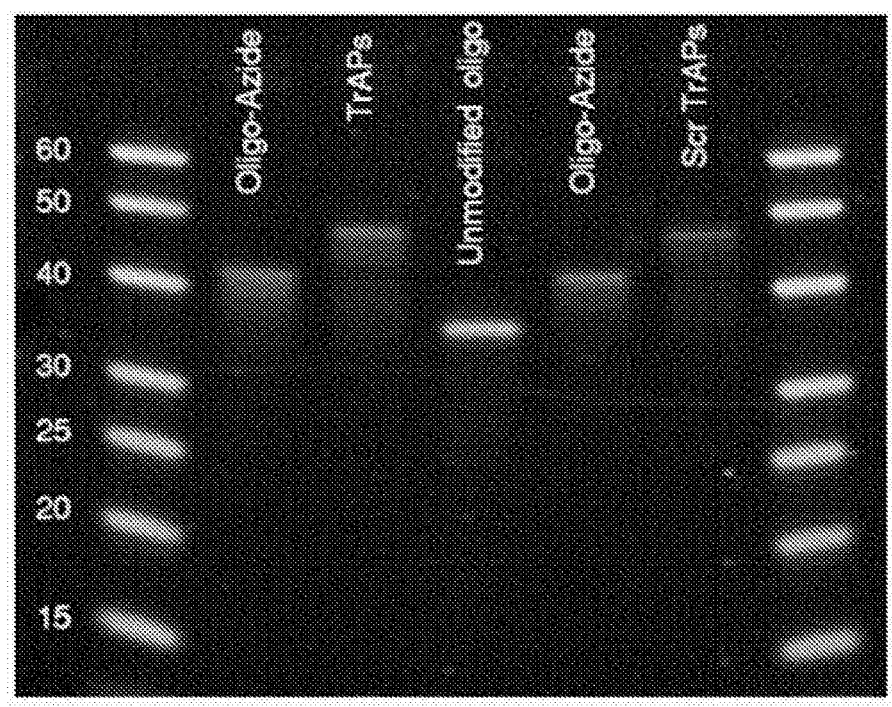
FIG. 11 shows the results of an experiment used to characterise the nucleic acid components of the TrAP constructs of the invention.

FIG. 11 shows some characterisation of the ssDNA aptamer used to create the construct. FIG. 11 (a) shows UV absorbency data for four samples of this DNA and demonstrate that the absorbance ratios are very similar for all samples suggesting a consistent and stable product. (data obtained from a NanoDrop photospectrometer)

FIG. 11 (b) is an image of a TBE-Urea denaturing cell which resolves as a characteristic band, respectively, the DNA aptamer ("Oligo-Azide"), the complete construct ("TrAPs"), the unmodified oligo, the DNA aptamer (replicate) and the complete construct having a scrambled peptide ("Scr TrAPs")

Example 2

The Monte Carlo binding simulation was run using the Igor Pro software and is based on competitive unbinding events using the Bell model of failure of molecular bonds under an applied force (DOI: 10.1126/science.347575 and 10.1146/annurev.biophys.30.1.105). Biophysical constants were taken from two journal articles (DOI: 10.1126/science.1151298 and 10.1529/biophysj.104.045690). The model calculates the unbinding rates for the binding between VEGF and the controlled release construct described in example 1 and also the unbinding rate for the binding between the an integrin and an integrin binding protein. FIG. 2(d) shows the two unbinding rates relative to each other across a wide range of tensional forces and shows that the controlled release constructs will unfold releasing VEGF ("aptamer unfolding") at a far greater rate than will be integrin dissociate from its binding partner ("integrin unbinding").

Example 3

This example demonstrates that constructs of the invention ("TrAPs") may be readily conjugated to collagen gels. FIG. 4 illustrates diagrammatically the conjugation strategy used. As illustrated in FIG. 4 (i) collagen contains free amines that may be functionalised with a linked such as the NHS-PEG2-maleimide linker illustrated. A DNA TrAP construct was synthesized by conventional oligonucleotide manufacturing techniques and made with a terminal thiol modification. As supplied such modified oligonucleotides are typically supplied with the sulphur atoms reduced to a S=S dithiol group for protection. This group may be reduced by the use of TCEP (tri(2-carboxyehyl)phosphine) to form a —SH group on the oligonucleotide terminus. FIG. 4 (ii) illustrated the reaction between the functionalised collagen and the thiol-TrAP constructs which are incubated together and react to bind the TrAP construct to the collagen matrix.

Figure 5:
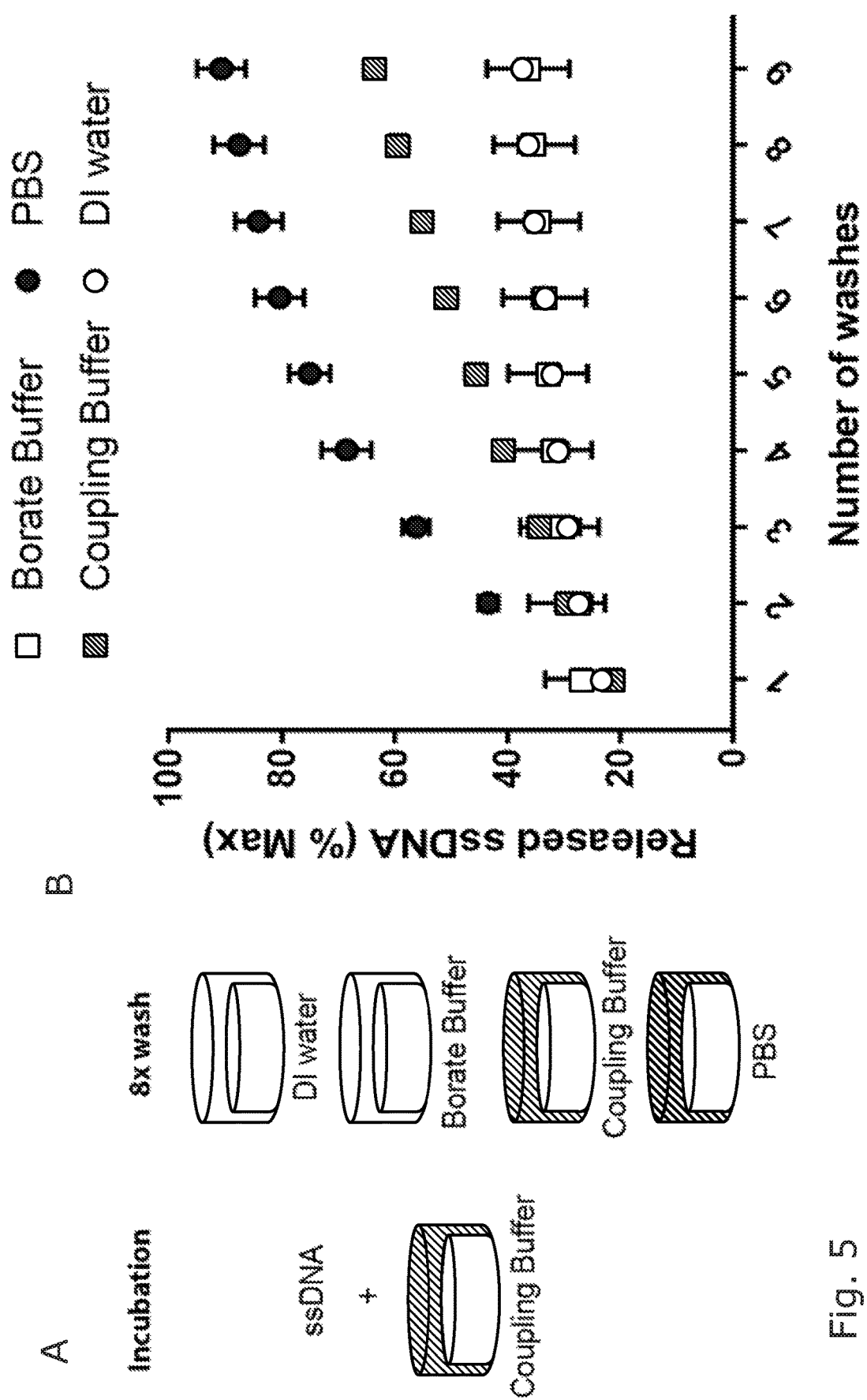
FIG. 5 illustrates the development of an optimal conjugation strategy for molecular complexes of the invention in part A. In part B there are presented data relating to the optimisation.

FIG. 5 illustrates an experiment carried out to optimise the conjugation strategy illustrated in general in FIG. 4. It is necessary to remove unconjugated DNA construct from the collagen matrix prior to growth factor loading of the construct. FIG. 5A illustrates the incubation stage wherein the ssDNA construct is incubated with the functionalised collagen in a coupling buffer. After coupling has been completed excess uncoupled construct is washed off 8 times using deionised water (DI water), a borate buffer, the coupling buffer or PBS (phosphate buffered saline). FIG. 5B shows that the optimal buffer to wash away unreacted ssDNA construct is PBS.

FIG. 6 illustrates an experiment carried out to demonstrate that a TrAP construct can be successfully linked to the collagen matrix. As illustrated in FIG. 6A the thiol-DNA construct was incubated with both maleimide-functionalised collagen and plain collagen. After washing x 8 with PBS buffer both types of material where incubated with an antisense ssDNA oligo (having sequence (IRD 700-GAAC-CACTGCACTCTAGTCTAAAT (SEQ ID NO: 6)) conjugated to the red fluorochrome IRD700 as a label.

In order to confirm that conjugation had occurred, the collagen matrices were sectioned and imaged using a wide field fluorescence microscope. FIG. 6B shows the images produced. The first row of three images corresponds to the maleimide-functionalised matrix and the second row of images corresponds to the control plain collagen matrix. The left hand images are fluorescent images and red fluorescence appears in the original in red and in this monochrome reproduction in a lighter shade.

The middle images are phase contrast images of the cells and the right hand images are a composite of the other two images. As can be seen from the images, only matrix which was previously functionalised with maleimide chemistry was able to react with the thiol-DNA construct.

Example 4

This example demonstrates that constructs of the invention ("TrAPs") may be readily conjugated to amino functionalised glass surfaces (coverslips).

Figure 7A:
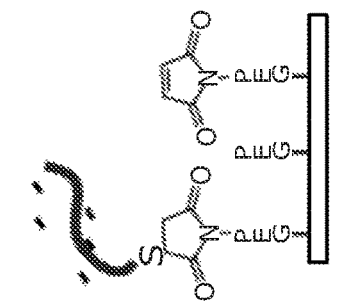
FIG. 7 illustrates that the constructs of the invention may be attached to functionalised glass surfaces.
Figure 7A:
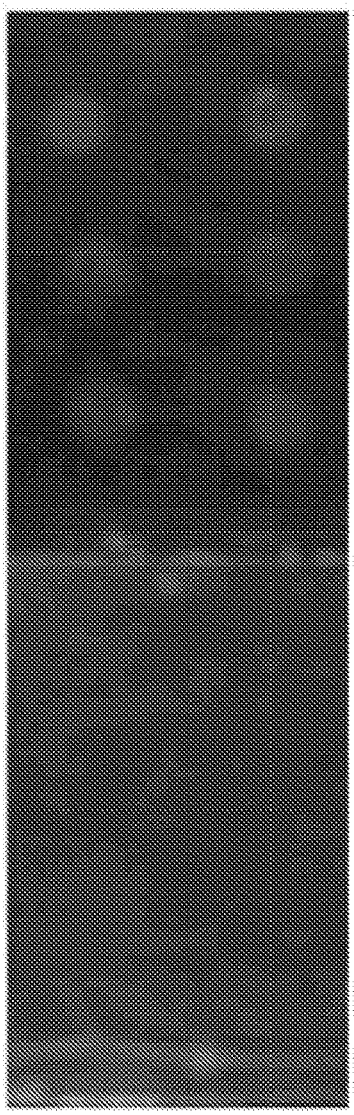
Figure 7A:
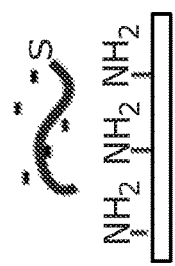
Figure 7B:
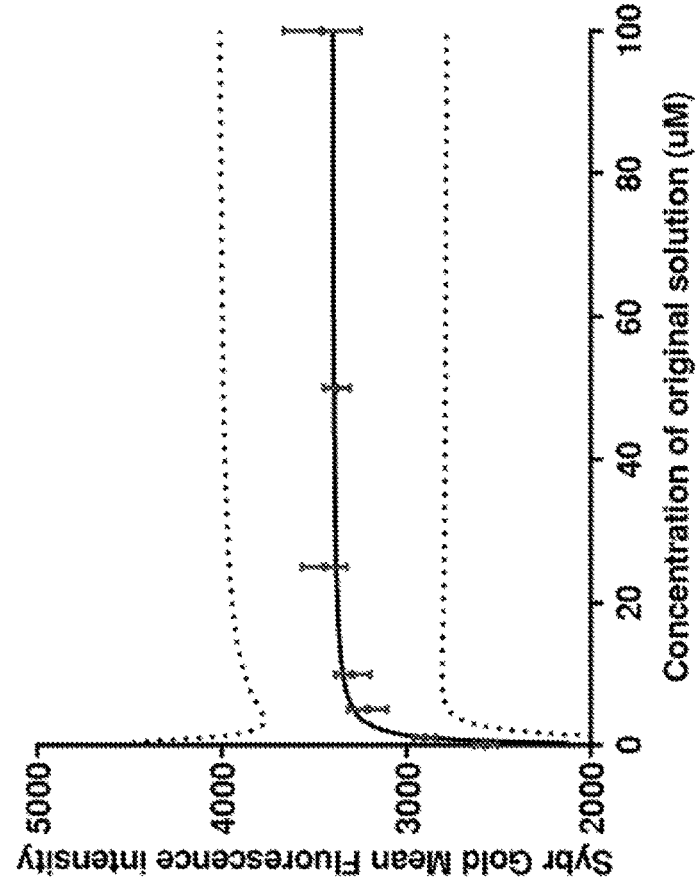
Figure 14A:
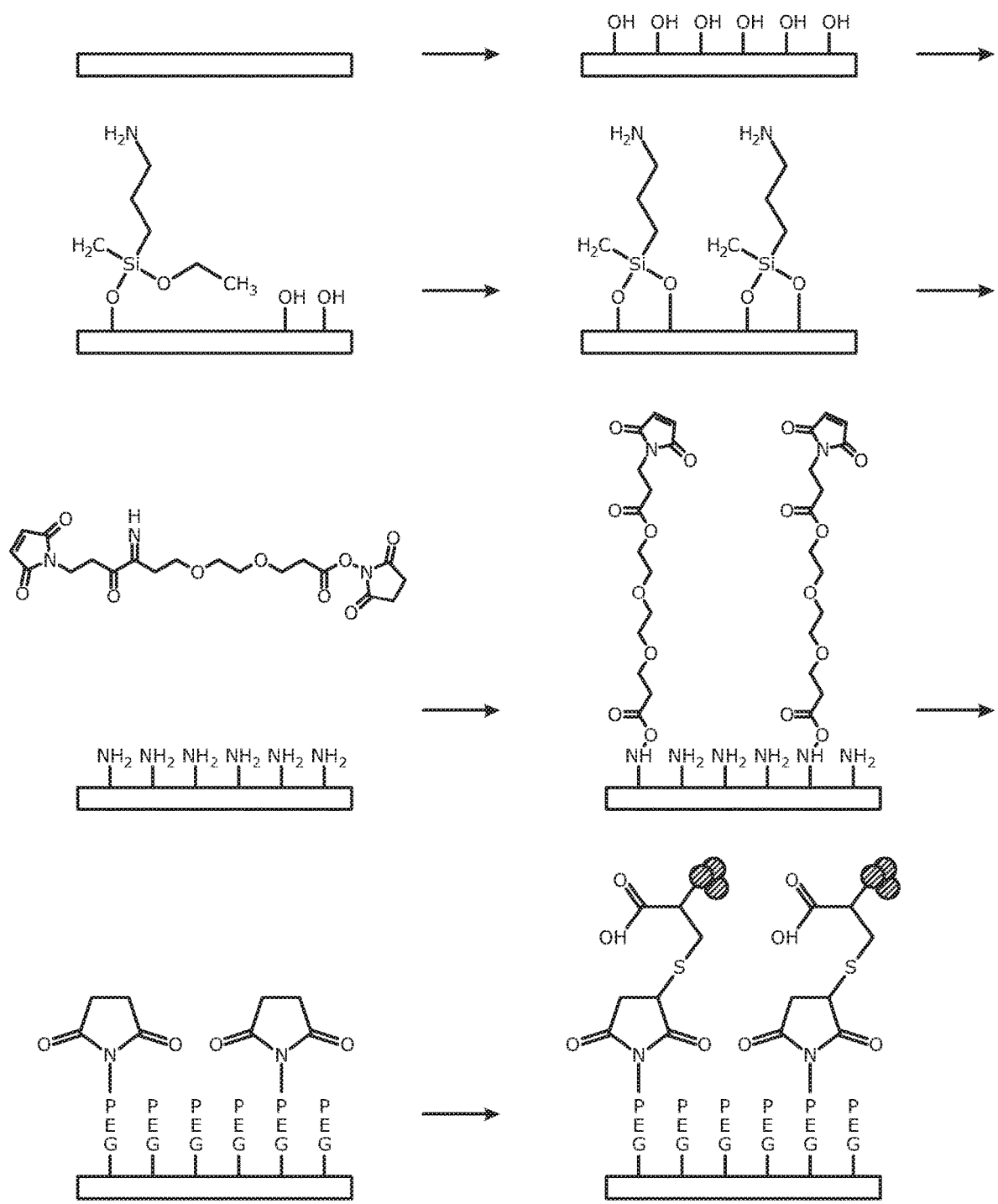
FIG. 14 illustrates an experiment demonstrating the functionalisation of a glass surface.
Figure 14B:
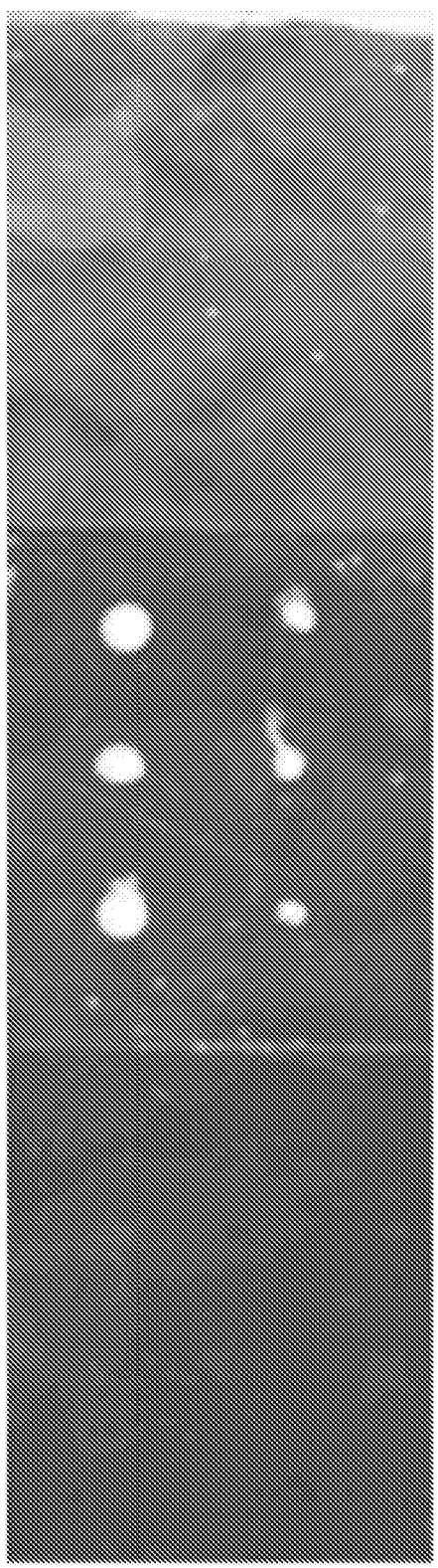

FIG. 7A illustrates the reaction scheme which is similar to that employed in Example 3, namely the reaction of a thio-DNA construct with an amino functionalised glass surface which has been maleimide functionalised or not. The DNA was visual using Sybr Gold staining and appropriate illumination, which identifies double stranded DNA. The images in FIG. 7A show that fluorescence is visible (as lighter shaded dots) in the maleimide functionalised surface but not the untreated surface. The data shown in FIG. 7B demonstrates that the extent of surface coverage increases with increasing concentration of the conjugating solution. Further information regarding a possible reaction scheme suitable for the functionalisation of glass surfaces is presented in FIG. 14 (a). FIG. 14 (b) demonstrates successful conjugation of TrAPs (as detected by the labelled antisense oligo used in Example 3) when following this reaction scheme.

Example 5

Glass coverslips were conjugated with TrAP constructs having a cell adhesion site which is either the RGD cell adhesion promoting peptide ("TrAPs"), or the scrambled RDG peptide ("scrambled TrAPs"), or, as a control, with cysteine. The TrAP constructs were loaded with VEGF as described in more detail in Example 1. The coverslips were then seeded with human microvasculature endothelial cells 1 (HMEC-1). Cells were imaged after staining with the CellTracker fluorescent dye and proliferation was measured using the PrestoBlue metabolic assay and a plate reader. FIG. 8A shows that cells on the surface conjugated to scrambled TrAP constructs the cells were predominantly round in morphology indicating that they had not adhered to the surface. Cells on the surface conjugated to unscrambled TrAP constructs showed a spreading morphology indicating the presence of focal adhesions. FIG. 8B shows the quantified proliferation and shows that cell number son TrAP functionalised surfaces were significantly higher than those on surfaces functionalised with scrambled TrAP and those functionalised with cysteine. This demonstrates that the VEGF is more proliferative on the cells when provided bound to an aptamer from which it can be released by cell adhesion and movement than when bound to an control construct from which it is less accessible because said control construct lacks the cell adhesion RGD sequence. N.S.=p 0.9937; cysteine versus TrAPs p=0.0144; scrambled TrAPs versus TrAPs p=0.0181; n=7; 1-way ANOVA with Tukey post-hoc testing.

Example 6

This example demonstrates that VEGF which is conjugated to the aptamer construct of the invention is held in an inactive form. The ssDNA aptamer sequence used is:

```
                                        (SEQ ID NO: 5)
AGGGCCACGTCTATTTAGACTAGAGTGCAGTGGTTC (K_D 0.20 nM)
```

Figure 12A:
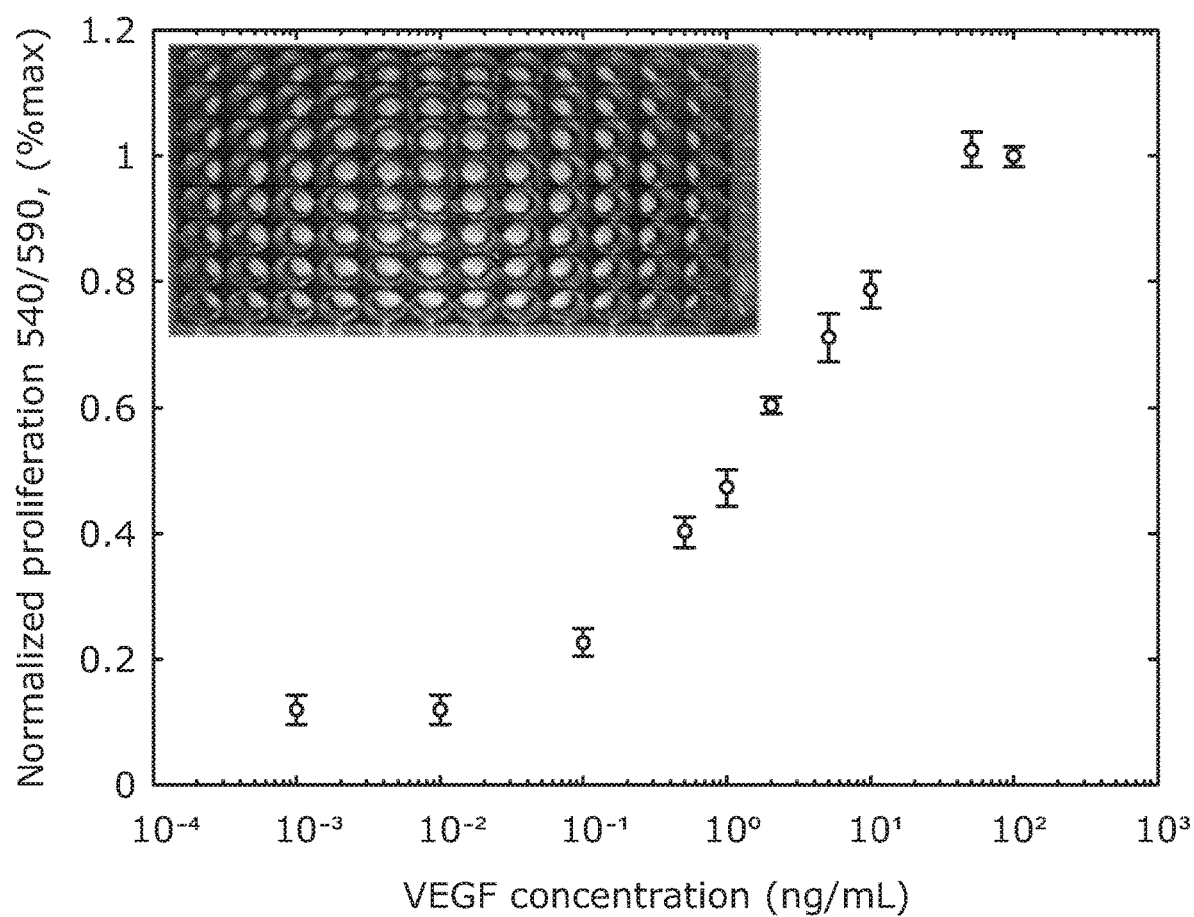
FIG. 12 shows the results of a proliferation experiment wherein it is demonstrated that when VEGF is bound to a TrAP construct according to the invention it is held in an inactive state.
Figure 12B:
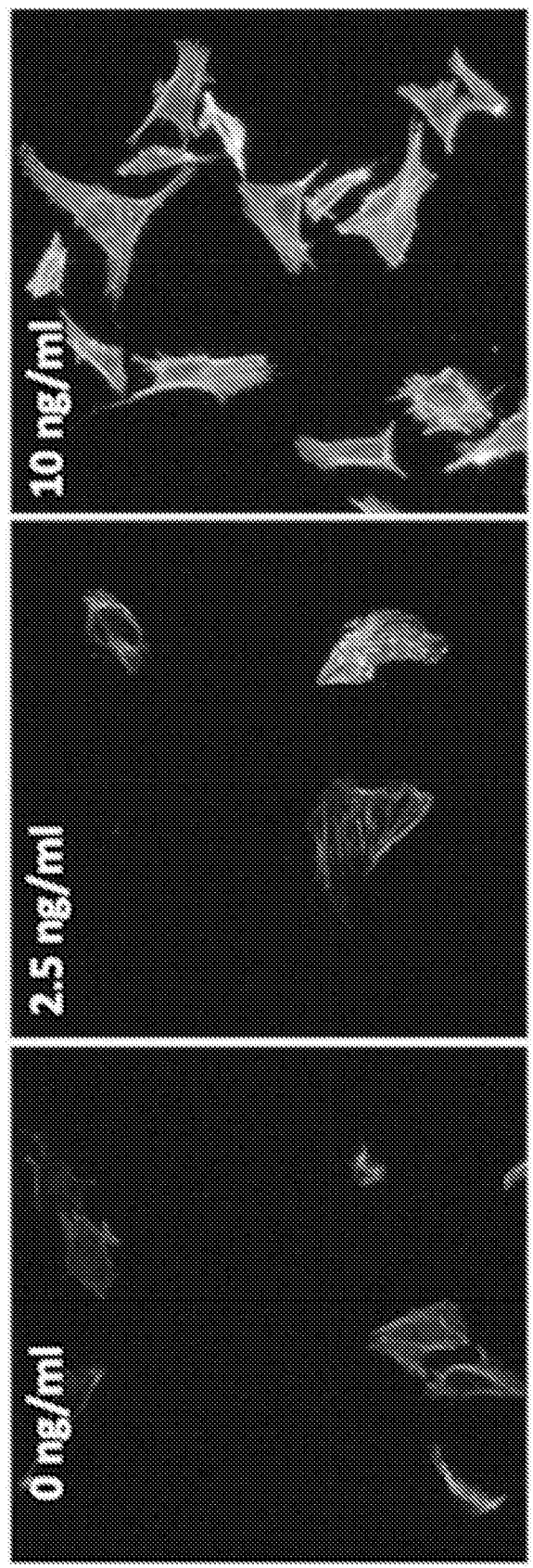
Figure 12C:
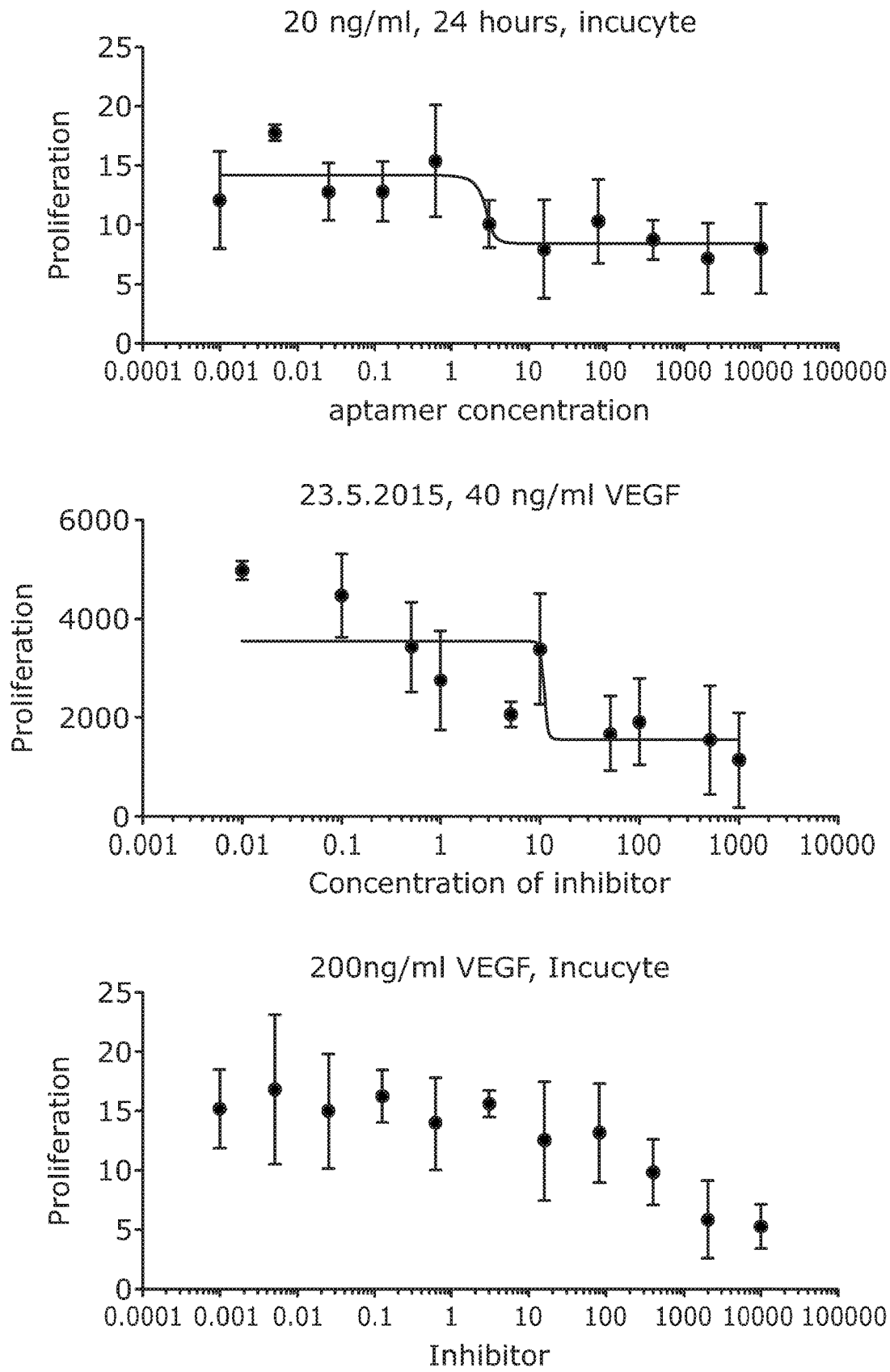

FIG. 12 (a) demonstrates that the endothelial cell line HUVECs proliferates in response to VEGF. The figure provides the baseline dose response curve for that cell type. FIG. 12 (b) illustrates in three photographs that the cells have more prominent actin cytoskeletons when exposed to VEGF. Cells were seeded at 10000 cells per well and left to adhere overnight in serum starved medium (0.1% FBS, L-Glu, PenStrep, HMEC-1 medium). VEGF and the aptamer DNA oligo were pre-mixed at various concentrations and pipetted onto the serum starved cells. The data shown in FIG. 12 (c) demonstrates that the aptamer sequence inhibited proliferation in a dose-dependent manner. This experiment allows the concentrations of VEGF and aptamer needed to enable complete VEGF sequestration to be identified.

Example 7

Figure 13A:
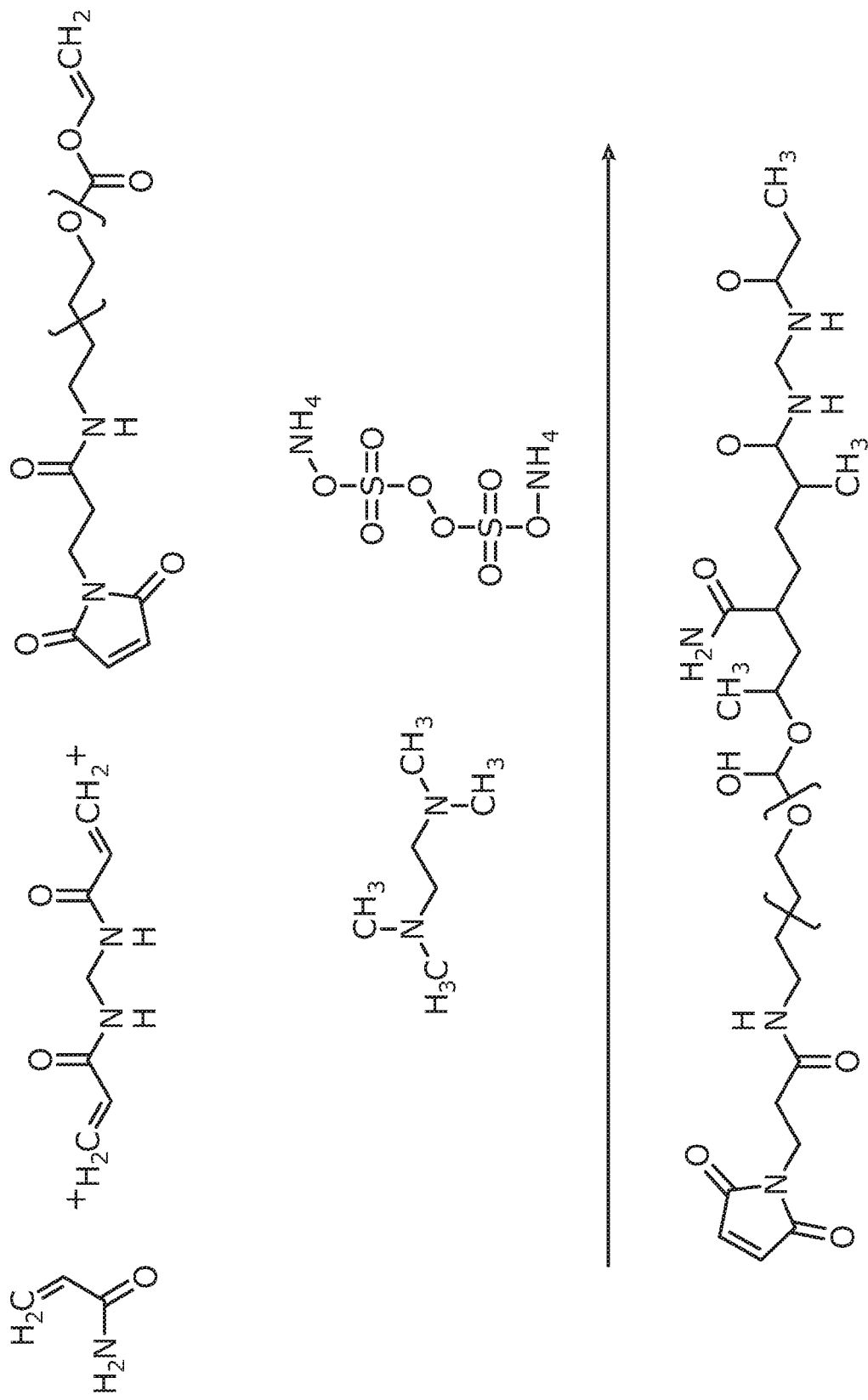
FIG. 13 shows the results of an experiment carried out to optimise the functionalisation of surfaces using a maleimide linker.
Figure 13B:
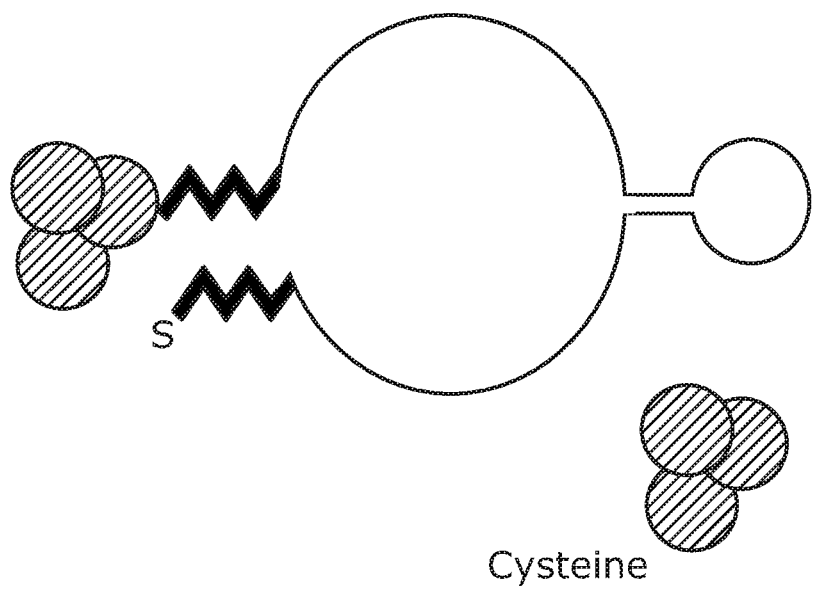
Figure 13B:
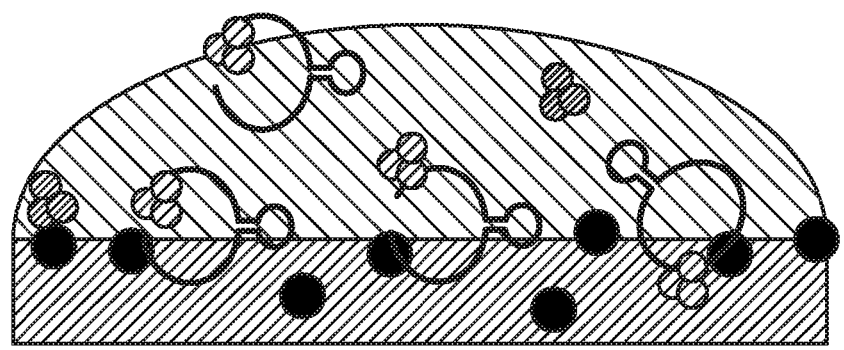
Figure 13:
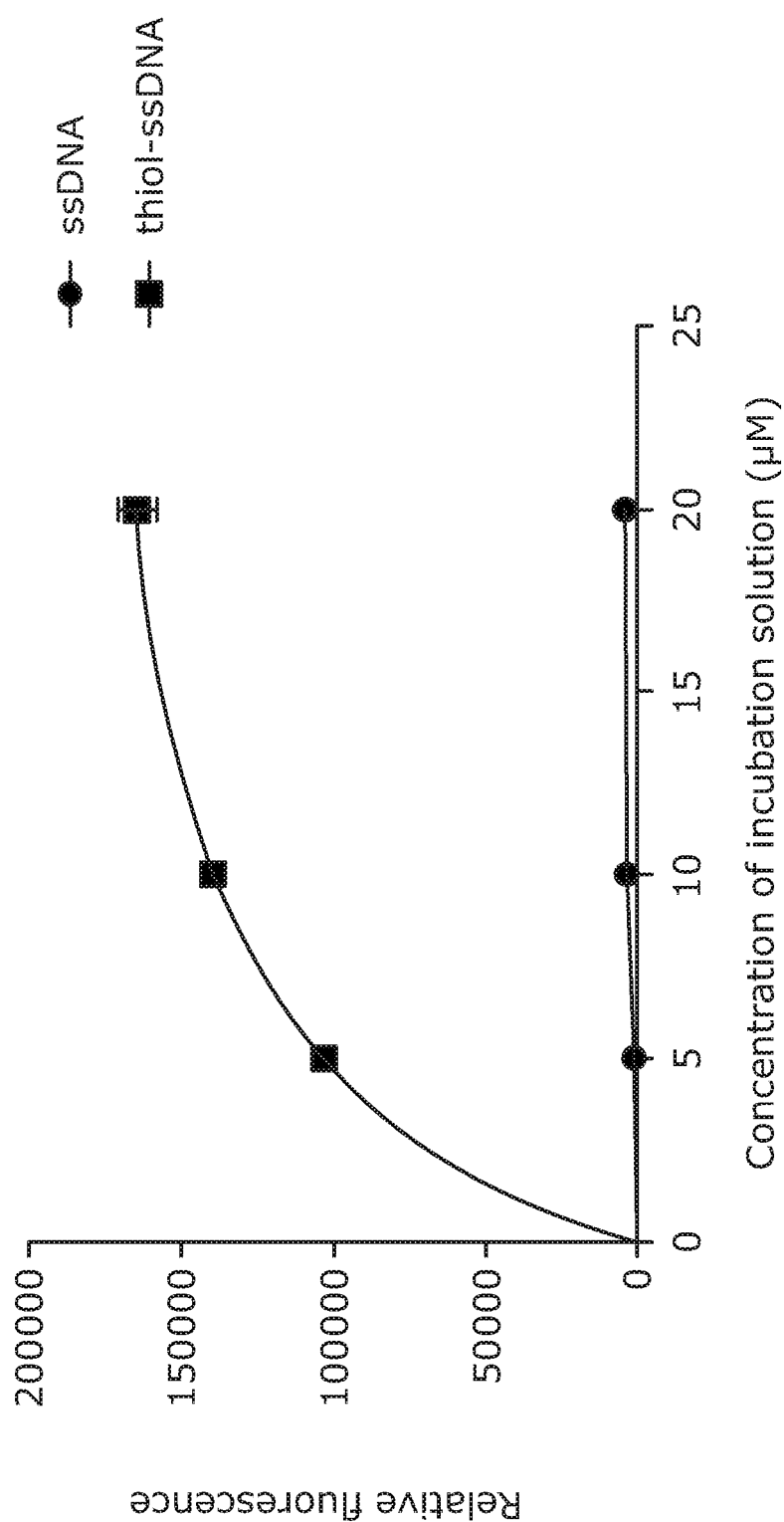

This example investigates the conjugation of constructs of the invention (TrAPs) to a polyacrylamide matrix. FIG. 13 (a) is a reaction scheme wherein maleimide groups can be incorporated into polyacrylamide gel during its polymerisation. Acrylate-PEG-maleimide linker is used to achieve this. The TrAP construct is then incubated with the functionalised gel as illustrated diagrammatically in FIG. 13 (b). This incubation step allows the user to fine tune the final concentration of the construct in the gel as show in FIG. 13(c) which demonstrates that the concentration of TrAP in the gel (as measured by a labelled anti-sense oligo as in Example 3) rises in dependence of the concentration of the incubating solution. The graph also shows as a negative control that virtually no DNA aptamer is captured in the gel when unless it is functionalised to conjugate with the gel (in this case by virtue of a terminal thiol group).

Example 8

Figure 9A:
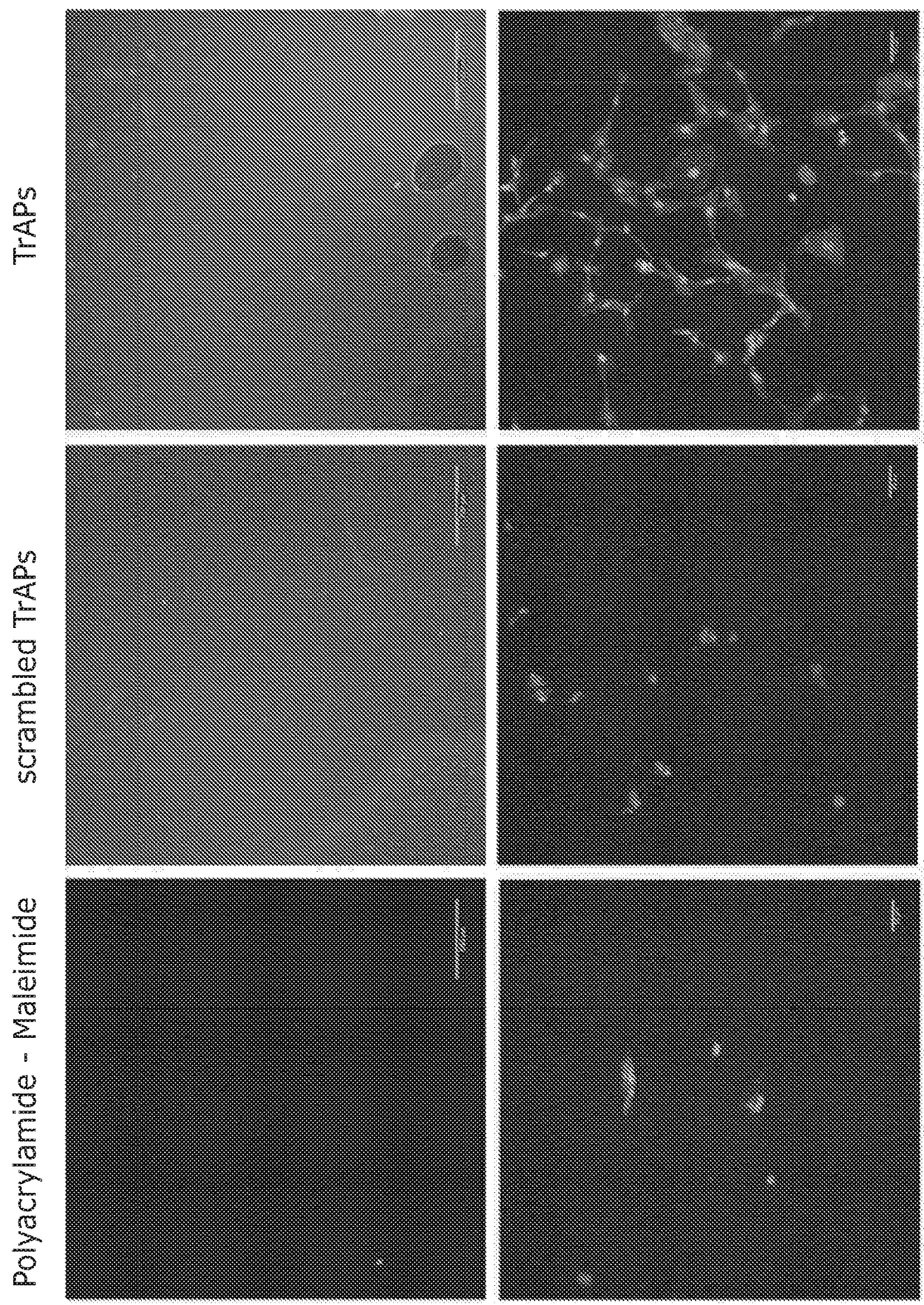
FIG. 9 illustrates an experiment demonstrating that cells adhere more to a polyacrylamide gel when functionalised with constructs of the invention. 9˚shows fluoresce micrographs which show cells in the red channel in the colour original (shown by a lighter shade in this monochrome reproduction).
Figure 9B:
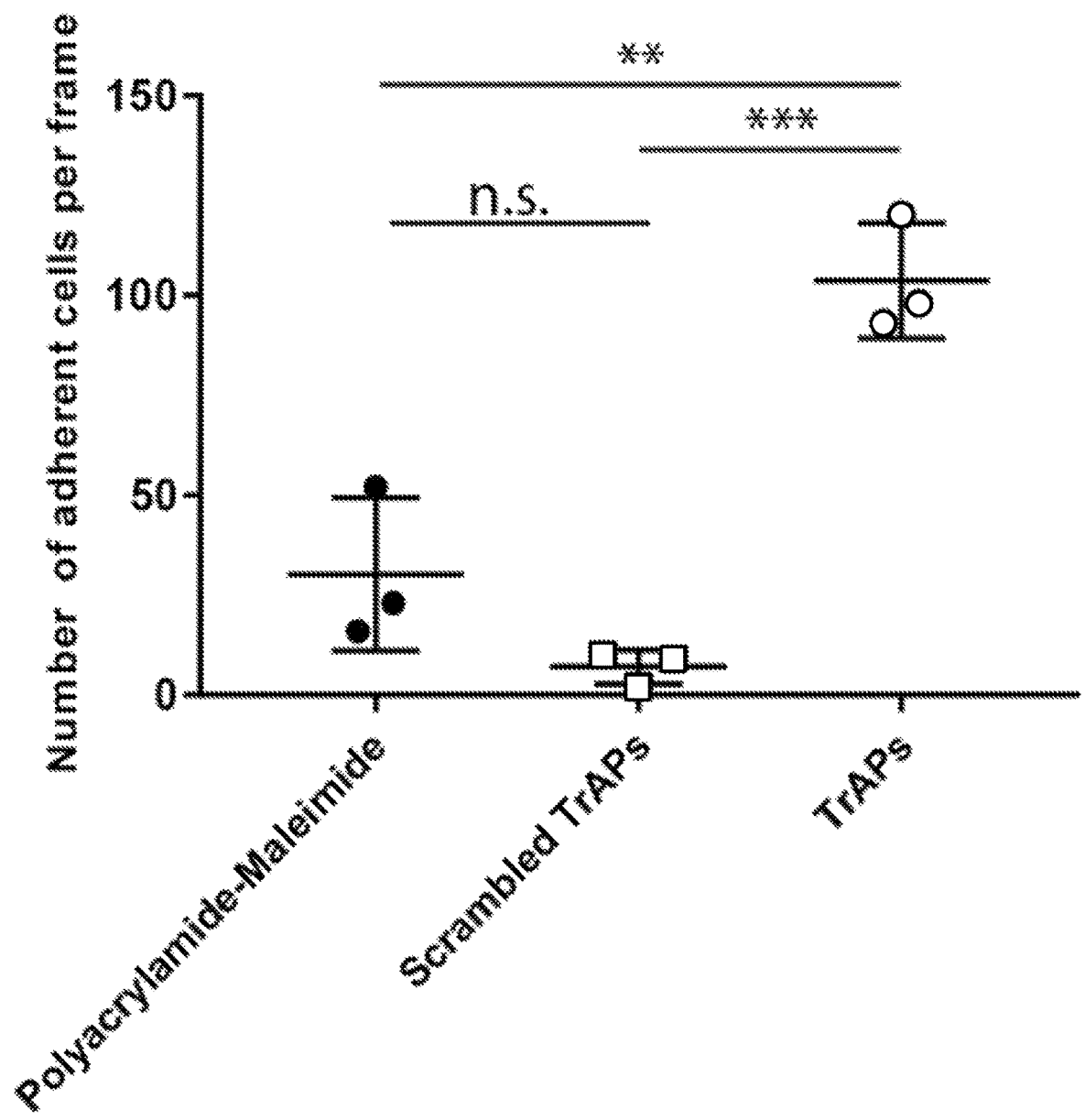

This example demonstrates that functional TrAP constructs can also be conjugated to polyacrylamide gels. As previously, the presence of TrAP construct was visualised using anti-sense oligos labelled with IRD700. FIG. 9A illustrates that only cells cultured with surfaces to which functional TrAP was conjugated can spread and adopt an adherent non-round morphology. FIG. 9B shows that a significantly higher number of cells adhered to surfaces conjugated with functional TrAP. Brightfield images were quantified (n.s. p=0.1838;  p=0.0017; * p=0.0004; n=3)

Example 9

Figure 15A:
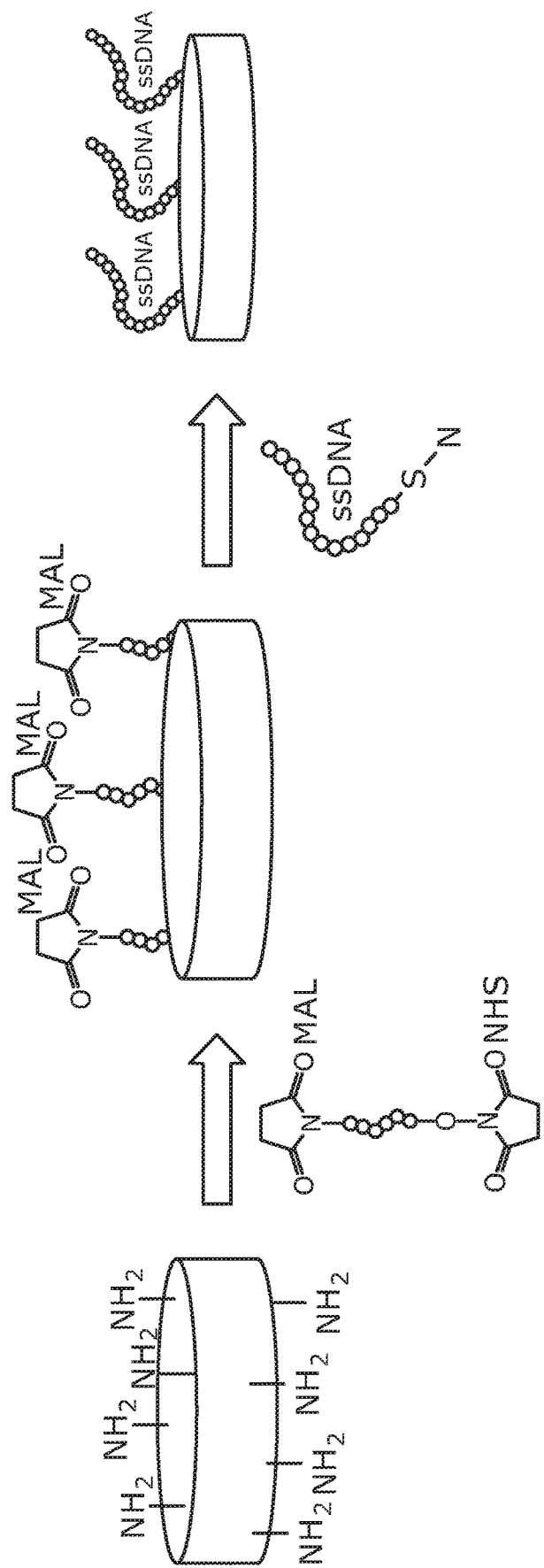
FIG. 15 illustrates an experiment exploring the conjugation of a three dimensional matrix with TrAP constructs of the invention.
Figure 15B:
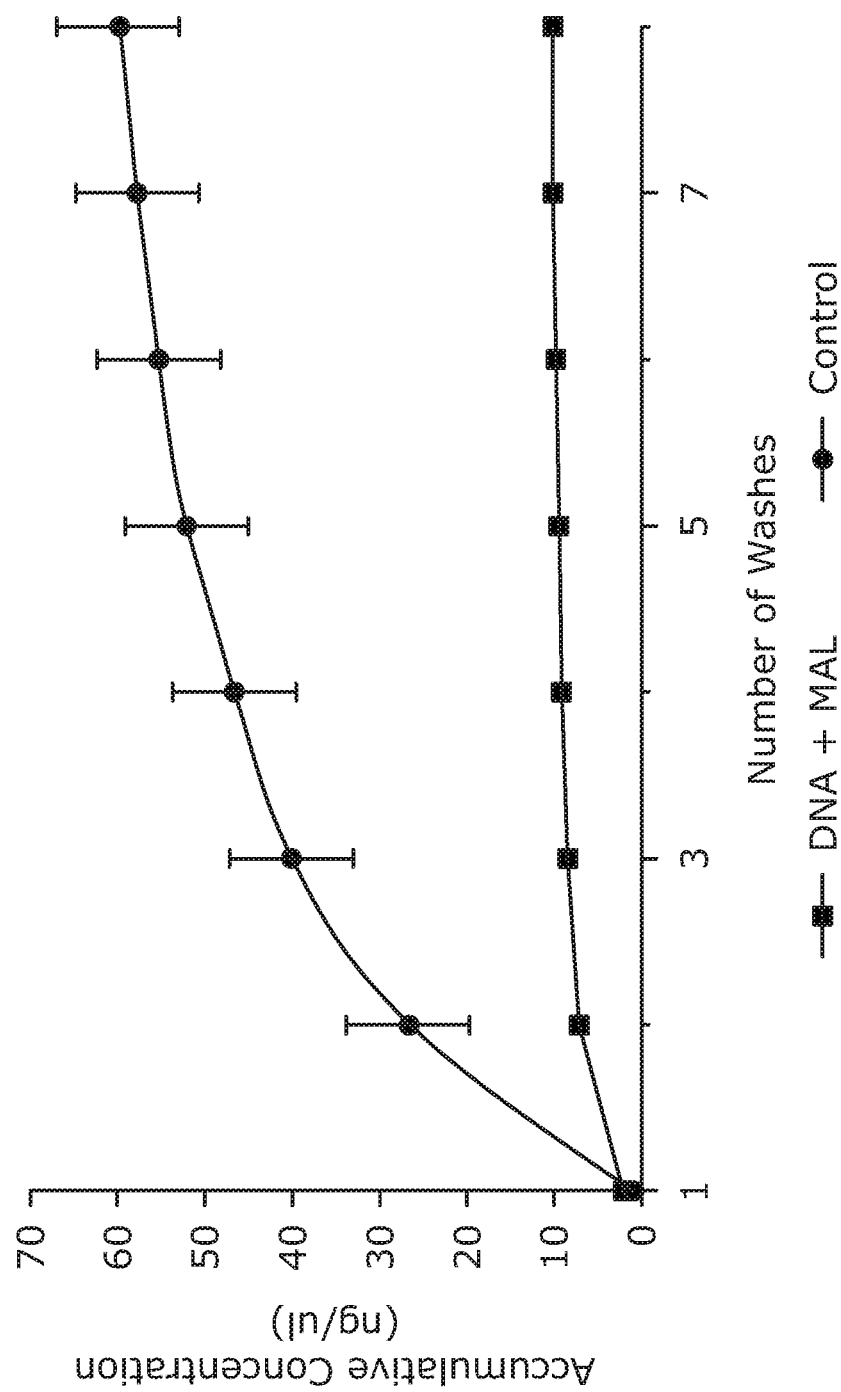
Figure 15:
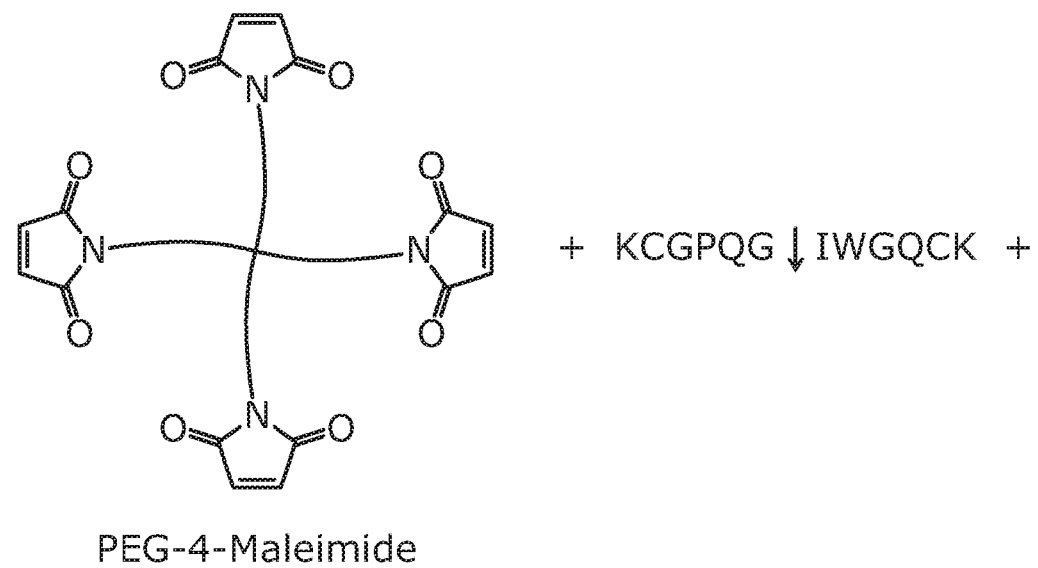
Figure 15:
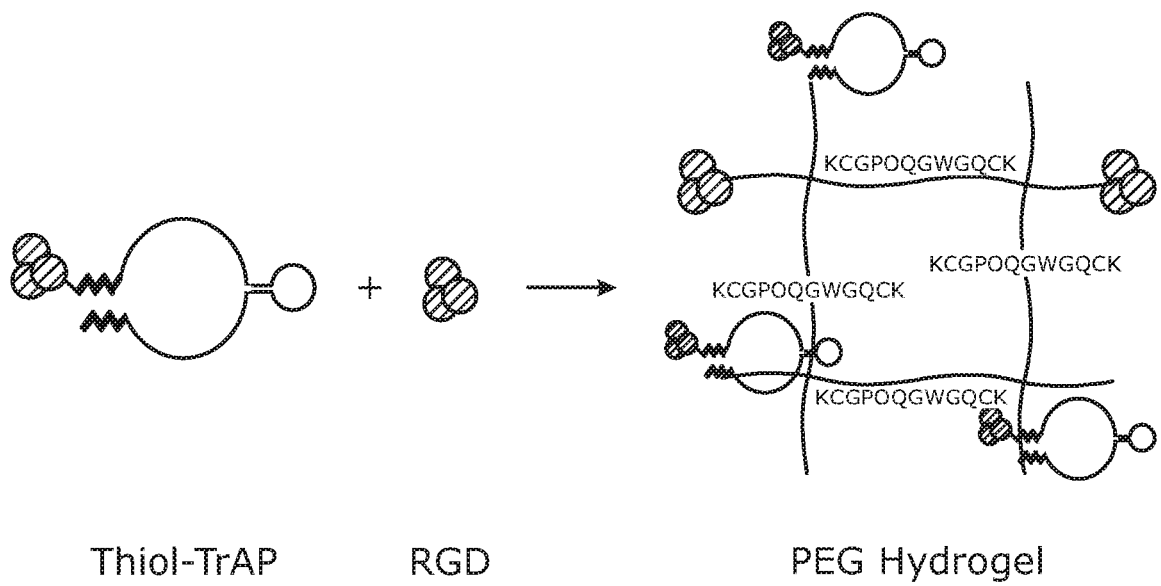

This example demonstrates a possible reaction scheme for the introduction of constructs into a natural 3D scaffold such as collagen and other artificial gels such as PEG gels. FIG. 15 (a) presents a reaction scheme for collagen gels and FIG. 15 (c) presents a reaction scheme for PEG gels (the dark balls are the amino acid residues forming the peptide which constitutes the cell binding site; the annotation KCGPQGIWGQCK is used to represent a peptide having a sequence capable of co-polymerising with the PEG-4 maleimide monomer. The sequence may also be shown as KCGPQG↓IWGQCK (SEQ ID NO: 7). It is designed to be degraded by matrix metalloproteases at the position indicated by the arrow). FIG. 15 (b) shows that the construct can be washed into the gel shown in FIG. 15 (a) by successive washes.

SEQUENCE LISTING

This specification is accompanied by a machine readable sequence listing according to WIPO Standard ST.26 which contains the following sequences (in 5' to 3'(or N- to C-terminal) order):

```
                                        (SEQ ID NO: 1)
Arg-Gly-Asp-D-Phe-Cys (SEQ ID NO: 2)
Arg-Ala-Asp-D-Phe-Cys (SEQ ID NO: 3)
Gly-Arg-Gly-Asp-Ser (SEQ ID NO: 4)
Gly-Arg-Gly-Asp-Ser-Pro (SEQ ID NO: 5)
AGGGCCACGTCTATTTAGACTAGAGTGCAGTGGTTC (SEQ ID NO: 6)
(IRD 700)-GAACCACTGGACTCTAGTCTAAAT (SEQ ID NO: 7)
Lys-Cys-Gly-Pro-Gln-Gly-Ile-Trp-Gly-Gln-Cys-Lys
```

The invention claimed is:

1. A molecular complex comprising:
a therapeutic agent; and
a controlled release construct, the controlled release construct comprising:
a primary matrix conjugation site which is linked to a cell adhesive site, via a binding region comprising an aptamer and optionally via one or more spacer elements, and
wherein the primary matrix conjugation site is for a naturally-occurring extracellular matrix or a component thereof, a biocompatible polymer, implantable collagen sponge, injectable filler, implantable nerve guidance conduits, extracellular thrombus, laboratory plastic ware or a coating thereof, glassware or a coating thereof, or an implantable medical device or part thereof.

2. A molecular complex as claimed in claim 1, wherein the construct further comprises a secondary matrix conjugation site linked to the cell adhesive site via a cleavage site but not via the binding region.

3. A molecular complex as claimed in claim 2, wherein the cleavage site is a site of enzymatic cleavage such that, when cleaved, the secondary matrix conjugation site is separated from the rest of the construct.

4. A molecular complex as claimed in claim 1, wherein the aptamer comprises a nucleic acid or derivative/analogue thereof.

5. A molecular complex as claimed in claim 4, wherein the aptamer comprises RNA, DNA, PNA (peptide nucleic acid), LNA (locked nucleic acid), BNA (bridged nucleic acid), MNA (morpholine nucleic acid), GNA (glycol nucleic acid) and TNA (threose nucleic acid), or a mixture thereof.

6. A molecular complex as claimed in claim 5, wherein the binding region aptamer comprises RNA, which RNA is optionally substituted.

7. A molecular complex as claimed in claim 5, wherein the aptamer consists of a single strand of nucleic acid or nucleic acid analogue.

8. A molecular complex as claimed in claim 5, wherein the binding region consists of a double stranded nucleic acid or nucleic acid analogue.

9. A molecular complex as claimed in claim 1, wherein the therapeutic agent is a protein growth factor.

10. A molecular complex as claimed in claim 1, wherein the therapeutic agent is a cytotoxic drug, for example, a nucleic acid intercalating agent such as daunomycin, doxorubicin or thalidomide.

11. A molecular complex as claimed in claim 1, further comprising an implantable matrix structure to which the matrix conjugation site or sites, is/are attached.

12. A molecular complex as claimed in claim 1, wherein the cell adhesive site comprises an integrin binding site.

13. A controlled release construct comprising:

a primary matrix conjugation site which is linked to a cell adhesive site via a binding region comprising an aptamer, and optionally via one or more spacer elements, and wherein the primary matrix conjugation site is for a naturally-occurring extracellular matrix or a component thereof, a biocompatible polymer, implantable collagen sponge, injectable filler, implantable nerve guidance conduits, extracellular thrombus, laboratory plastic ware or a coating thereof, glassware or a coating thereof, or an implantable medical device or part thereof.

14. A pharmaceutical composition comprising a molecular complex as defined in claim 1 and a pharmaceutically acceptable carrier.

15. A method of delivery of a therapeutic agent to a subject in need thereof, comprising administering a molecular complex as defined in claim 1 to said subject.

16. A method of treating a subject in need of tissue regeneration comprising administering a molecular complex as defined in claim 1 to said subject.

17. A method of making a molecular complex as defined in claim 1 comprising:

contacting a therapeutic agent with the controlled release construct as defined in claim 1.

18. A pharmaceutical composition comprising a controlled release construct as defined in claim 13 and a pharmaceutically acceptable carrier.

19. A method of delivery of a therapeutic agent to a subject in need thereof, comprising administering a molecular complex as defined in claim 1 to said subject.

20. A molecular complex as claimed in claim 1 wherein the therapeutic agent is VEGF-A, VEGF-B, VEGF-C, or VEGF-D.

* * * * *

SEQUENCE LISTING

<160> NUMBER OF SEQ ID NOS: 9

<210> SEQ ID NO 1
<211> LENGTH: 5
<212> TYPE: PRT
<213> ORGANISM: Artificial sequence
<220> FEATURE:
<223> OTHER INFORMATION: synthetic sequence

```
<220> FEATURE:
<221> NAME/KEY: MISC_FEATURE
<222> LOCATION: (4)..(4)
<223> OTHER INFORMATION: The residue is D-Phe

<400> SEQUENCE: 1

Arg Gly Asp Phe Cys
1               5

<210> SEQ ID NO 2
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: The residue is D-Phe

<400> SEQUENCE: 2

Arg Ala Asp Phe Cys
1               5

<210> SEQ ID NO 3
<211> LENGTH: 5
<212> TYPE: PRT
<213> ORGANISM: Artificial sequence
<220> FEATURE:
<223> OTHER INFORMATION: synthetic sequence

<400> SEQUENCE: 3

Gly Arg Gly Asp Ser
1               5

<210> SEQ ID NO 4
<211> LENGTH: 6
<212> TYPE: PRT
<213> ORGANISM: Artificial sequence
<220> FEATURE:
<223> OTHER INFORMATION: synthetic sequence

<400> SEQUENCE: 4

Gly Arg Gly Asp Ser Pro
1               5

<210> SEQ ID NO 5
<211> LENGTH: 36
<212> TYPE: DNA
<213> ORGANISM: Artificial sequence
<220> FEATURE:
<223> OTHER INFORMATION: synthetic sequence

<400> SEQUENCE: 5
agggccacgt ctatttagac tagagtgcag tggttc                                36

<210> SEQ ID NO 6
<211> LENGTH: 24
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide is conjugated to fluorochrome
      IRD 700

<400> SEQUENCE: 6
```

```
gaaccactgc actctagtct aaat                                              24

<210> SEQ ID NO 7
<211> LENGTH: 12
<212> TYPE: PRT
<213> ORGANISM: Artificial sequence
<220> FEATURE:
<223> OTHER INFORMATION: synthetic sequence

<400> SEQUENCE: 7

Lys Cys Gly Pro Gln Gly Ile Trp Gly Gln Cys Lys
1               5                   10

<210> SEQ ID NO 8
<211> LENGTH: 36
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (36)..(36)
<223> OTHER INFORMATION: The nucleotide is attached to a thiol group

<400> SEQUENCE: 8
agggccacgt ctatttagac tagagtccag tggttc                                 36

<210> SEQ ID NO 9
<211> LENGTH: 36
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (36)..(36)
<223> OTHER INFORMATION: The nucleotide is linked to a collagen matrix

<400> SEQUENCE: 9
agggccacgt ctatttagac tagagtccag tggttc                                 36
```